US011817212B2

(12) United States Patent
Hadorn et al.

(10) Patent No.: US 11,817,212 B2
(45) Date of Patent: Nov. 14, 2023

(54) MAINTENANCE METHOD FOR A LABORATORY SYSTEM

(71) Applicant: Roche Diagnostics Operations, Inc., Indianapolis, IN (US)

(72) Inventors: Maik Hadorn, Lucern (CH); Markus Bornhoeft, Kuessnacht am Rigi (CH); Herbert Schurtenberger, Goldau (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 815 days.

(21) Appl. No.: 16/907,605

(22) Filed: Jun. 22, 2020

(65) Prior Publication Data
US 2020/0411176 A1 Dec. 31, 2020

(30) Foreign Application Priority Data
Jun. 26, 2019 (EP) ..................................... 19182503

(51) Int. Cl.
*G16H 40/40* (2018.01)
*G16H 40/67* (2018.01)
(Continued)

(52) U.S. Cl.
CPC ............. *G16H 40/67* (2018.01); *G16H 40/40* (2018.01); *G06F 11/004* (2013.01); *G06N 7/01* (2023.01); *G16H 10/40* (2018.01)

(58) Field of Classification Search
CPC ............................... G16H 40/67; G16H 40/40
See application file for complete search history.

(56) References Cited

U.S. PATENT DOCUMENTS 5,508,826 A * 4/1996 Lloyd .................. H04N 1/6033
358/518
2014/0297344 A1* 10/2014 Beigel .............. G06Q 10/06311
705/7.13
(Continued)

FOREIGN PATENT DOCUMENTS

CN 107015895 A 8/2017
EP 3319026 A1 5/2018
(Continued)

OTHER PUBLICATIONS

Zapata Rivera, L. F. and Larrondo Petrie, M .; The Remote Laboratory Management System (RLMS) Pattern. jn 2, 3, Article 1 (May 2010), 9 pages. (Year: 2010).*

*Primary Examiner* — Joseph D Torres
(74) *Attorney, Agent, or Firm* — Roche Diagnostics Operations, Inc.

(57) ABSTRACT

A maintenance method for a laboratory system comprising a first and second group of laboratory instruments for processing biological samples, data collection components connected to the groups of instruments, and a remote maintenance system connected to the data collection components is presented. The method comprises collecting operational data from the laboratory instruments by the data collection components, detecting an anomaly related to the laboratory instruments by a first data collection component, transmitting context data to the remote maintenance system upon detection of an anomaly, determining correlation(s) between the operational data and the anomaly(s), validating the correlation(s), determining at the remote maintenance system predictive rules corresponding to validated correlations, transmitting the predictive rule(s) to the data collection components, and predicting occurrence of an anomaly of
(Continued)

laboratory instruments based on the one or more predictive rule(s) by the data collection components.

15 Claims, 8 Drawing Sheets

(51) Int. Cl.
    *G16H 10/40* (2018.01)
    *G06F 11/00* (2006.01)
    *G06N 7/01* (2023.01)

(56) References Cited

U.S. PATENT DOCUMENTS

| | | |
|---|---|---|
| 2015/0356457 A1 | 12/2015 | Ghosh et al. |
| 2016/0153806 A1 | 6/2016 | Ciasulli et al. |
| 2016/0321126 A1 | 11/2016 | Burugula et al. |
| 2016/0366209 A1 | 12/2016 | Netto et al. |
| 2017/0031803 A1 | 2/2017 | Wang et al. |
| 2017/0180214 A1 | 6/2017 | Azevedo et al. |
| 2017/0329813 A1 | 11/2017 | Fackelman et al. |

FOREIGN PATENT DOCUMENTS

| | | | |
|---|---|---|---|
| EP | 3425369 A1 | 1/2019 | |
| WO | WO-2013153237 A1 * | 10/2013 | ............... A01H 1/00 |

* cited by examiner

MAINTENANCE METHOD FOR A LABORATORY SYSTEM

CROSS-REFERENCE TO RELATED APPLICATIONS

This application claims priority to EP 19182503.3, filed Jun. 26, 2019, which is hereby incorporated by reference.

BACKGROUND

The present disclosure generally relates to a maintenance method for a laboratory system, a laboratory system configured to carry out the maintenance method, a computer program product which when executed by a remote maintenance system of a laboratory system causes the laboratory system to carry out the maintenance method.

With the rising complexity of laboratory instruments (such as pre-, post-, and analytical laboratory instruments, transportation systems or laboratory middleware) and laboratory systems, the modalities of addressing anomalies requiring some degree of intervention/maintenance is gaining more and more importance. In the context of the present disclosure, an anomaly relates to a failure of a laboratory instrument/system or system components and/or a deviation of the respective system or instrument from a status considered as normal respectively accepted operation. The normal respectively accepted operation is defined by one or more of: operating parameters/specification defined by the manufacturer/owner/regulatory body; statistically determined mean/average values of the respective operating parameters of identical or similar systems/instruments (peer comparison); and/or operation marked by an operator/technician/expert as normal operation.

One modality of addressing anomalies is by reactive maintenance, that is, as its name implies, by reacting to an anomaly that already happened. However, reactive maintenance is usually accompanied by downtime of the affected laboratory instrument/system, which impacts operation of the laboratory instrument(s) and even the entire laboratory system. Furthermore, reactive maintenance often leads to the need of emergency dispatch of a technician to remedy the anomaly since the reaction cannot be planned.

The occurrence of downtimes and the need for emergency dispatches of technicians is to some degree reduced by preventive maintenance. According to this approach, laboratory instruments/systems are maintained according to a set of recommendations on how to maintain the equipment based on insights from an engineering or R&D team that created the product. Often compliance with time-based maintenance requirements is required as part of leasing or warranty terms. However, preventive maintenance is only efficient for relatively predictable service activities. In addition, preventive maintenance introduces additional costs since, as its name implies, it is based on the concept of performing a maintenance task before it is actually required to prevent a foreseeable (at least to a certain degree of probability) anomaly. That means that components are exchanged, serviced, checked, and the like when the probability of an anomaly exceeds a certain threshold, a probability based on statistical data and not dependent on the actual state of the laboratory instrument/system. Hence, it could happen that for example spare parts that are still functional are exchanged due to the expiration of a pre-defined time period. This leads to significant unnecessary costs.

Condition-based maintenance addresses the disadvantages of preventive maintenance in that, instead of maintaining laboratory instruments/systems based on a pre-defined schedule, condition-based maintenance evaluates an asset's actual condition to determine the need for maintenance. With the automation of many industries and the widespread use of computers and sensors, condition-based maintenance has become more and more automated. Sensors that are part of or connected to laboratory instrument(s)/system(s) provide (real-time) data to remote maintenance systems that aid maintenance teams in maintaining equipment before anomalies occur.

In order to address shortcomings of reactive and preventive maintenance, predictive maintenance is based on the concept of actively predicting an anomaly specific to the respective laboratory instrument/system. Predictive maintenance takes condition-based maintenance a step further. Once operational data as well as data indicative of anomalies is available, advanced analytics are used to identify correlations between the operational data and the anomaly(s).

By applying analytics (expert driven and/or by machine learning) to data generated by the laboratory instrument(s)/system(s) to gain a better understanding of their condition, one can act on these as part of an improvement process. In other words, predictive maintenance uses data from the laboratory instrument(s)/system(s) to monitor parameters of the laboratory instrument(s)/system(s) and uses this data in conjunction with analyzed historical trends to (continuously) evaluate the system health and predict an anomaly before it happens. In addition, data beyond instruments can be used for predictions, such as environmental data, information from other systems (such as patient data), and any other data sources that may be valuable.

Known implementations of predictive maintenance have the common prerequisite of complete access to data in order for advanced analytics to be able to identify condition(s) of the laboratory instrument(s)/system(s) that could lead to an anomaly. However, the volume of data required for predictive maintenance poses a serious limitation. Complex laboratory systems comprise tens or even hundreds of instruments, each being characterized by dozens of operational parameters. The volume of data needed to be transmitted for analysis for predictive maintenance is enormous, which could lead to bottlenecks and possibly rendering advanced analytics impractical.

In order to reduce the volume of data transferred for advanced analytics, known solutions filter the data transferred from the laboratory. However, filtering the data used for determining the cause of an anomaly bears the risk that data relevant to the anomaly is not available.

In order to avoid the bottleneck of transferring large amounts of data and also the risks posed by filtering out potentially relevant data, according to another known proposed system, predictive maintenance is performed on-site.

In addition to limitations on the volume of data required for advanced analytics of predictive maintenance, restricted availability of data due to privacy concerns poses a further limitation on the applicability of predictive maintenance, in particular in the field of diagnostic laboratory systems handling sensitive data related to the health of patients, such as data indicative of a certain disease, condition, infection, and the like. In view of the sensitive nature of the data, operators of certain laboratory systems greatly limit or even prohibit any data from leaving the laboratory system. Furthermore, even if the data is allowed to leave the laboratory system, sometimes regulatory requirements limit or even prohibit data leaving a certain jurisdiction (e.g., beyond the borders of a state). In order to address this problem—limitations on the kind of data available for advanced analytics of predictive maintenance—according to a known proposal, predictive maintenance is provided within the boundaries of the region within which the sensitive data must be kept.

However, regardless whether due to data volume and/or data privacy limitations, local or regional implementations of predictive maintenance are unable to leverage the findings of advanced analytics enabled by large amounts of data. For example, rarely occurring anomalies might not be detected in a single locally implemented system before it already leads to the need for reactive maintenance. At the same time, it could happen that the same anomaly occurred at a different location in the past unbeknownst to any other location. Even a plurality of local or regional implementations of predictive maintenance would be unable to effectively predict such rare anomalies as these anomalies would only occur in isolated systems, each unable to recognize a pattern between certain operational data and the occurrence of the respective anomaly.

Therefore, there is a need for a maintenance method for a laboratory system addressing the drawbacks of reactive and preventive maintenance as well as the limitations of currently known implementations of predictive maintenance.

SUMMARY

According to the present disclosure, a maintenance method for a laboratory system is presented. The laboratory system can comprise a first group and a second group of laboratory instruments for processing biological samples, a plurality of data collection components communicatively connected to the first group and second group of laboratory instruments, and a remote maintenance system communicatively connected to the data collection components. The first group of laboratory instruments is connected to a first data collection component while the second group of laboratory instruments is connected to a second data collection component. The method can comprise collecting operational data from the laboratory instruments by the data collection components. The operational data can be indicative of one or more operational parameters of the respective laboratory instruments. The method can also comprise detecting an anomaly related to one or more of the plurality of laboratory instruments of the first group by the first of the plurality of data collection components based on the collected operational data and transmitting context data by the first of the plurality of data collection components to the remote maintenance system upon detection of an anomaly. The context data can comprise operational data and data indicative of the anomaly. The method can also comprise determining one or more correlation(s) between the operational data and the anomaly(s) at the remote maintenance system, validating the one or more correlation(s) at the remote maintenance system, determining at the remote maintenance system one or more predictive rules corresponding to validated correlations, transmitting the one or more predictive rule(s) by the remote maintenance system to the data collection components, and predicting occurrence of an anomaly of one or more of the plurality of laboratory instruments based on the one or more predictive rule(s) by one or more of the plurality of data collection components.

Accordingly, it is a feature of the embodiments of the present disclosure to provide a maintenance method for a laboratory system addressing the drawbacks of reactive and preventive maintenance as well as the limitations of currently known implementations of predictive maintenance. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
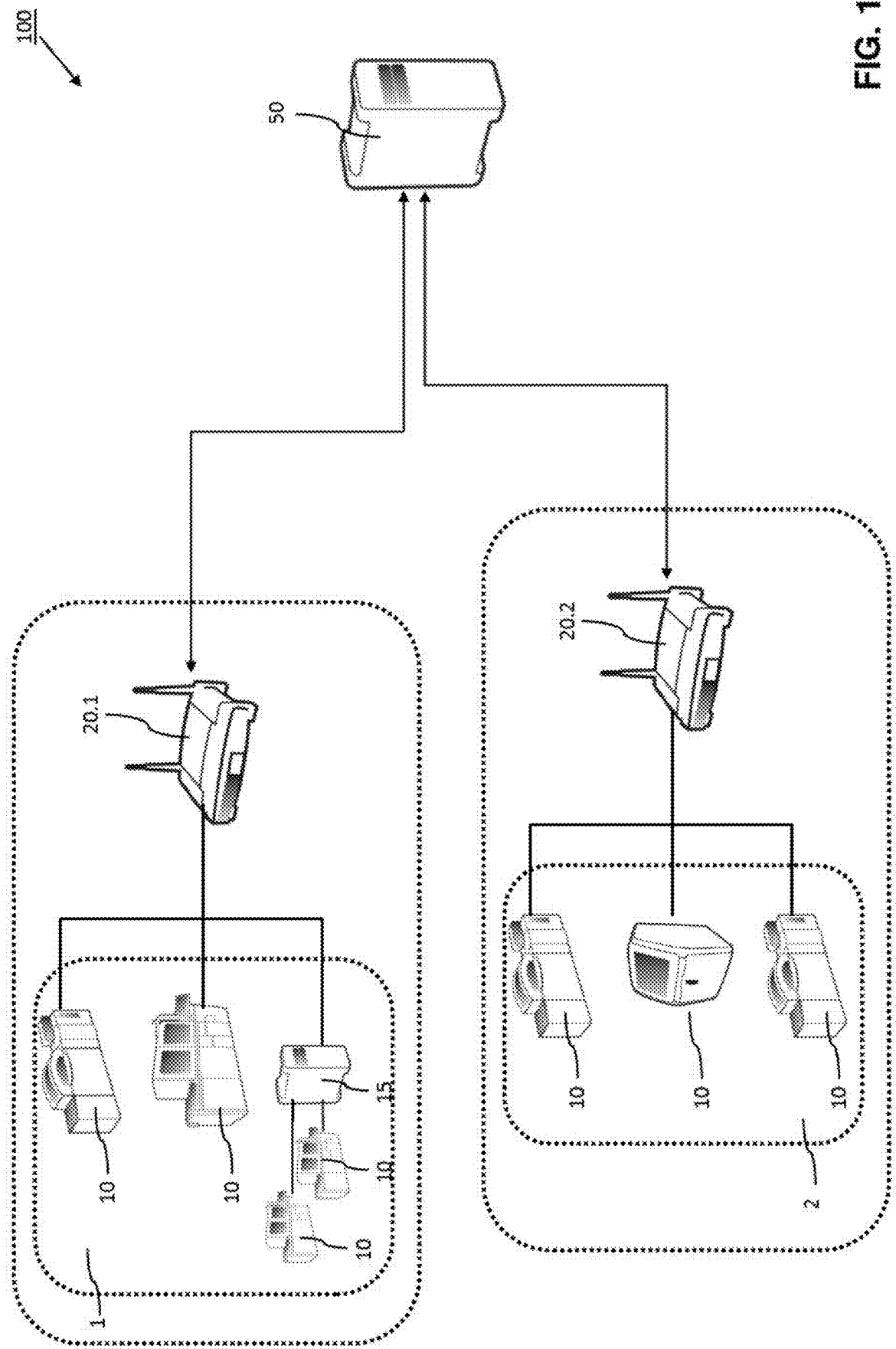
FIG. 1 illustrates a highly schematic block diagram of the disclosed laboratory system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The use of the 'a' or 'an' are employed to describe elements and components of the embodiments herein. This is done merely for convenience and to give a general sense of the inventive concepts. This description should be read to include one or at least one and the singular includes the plural unless it is obvious that it is meant otherwise.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term 'analyte' can be a component of a sample to be analyzed, e.g., molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence and/or concentration is intended. Examples of analytes can be glucose, coagulation parameters, endogenic proteins (e.g., proteins released from the heart muscle), metabolites, nucleic acids and so on.

The term 'laboratory instrument' as used herein can encompass any apparatus or apparatus component operable to execute and/or cause the execution of one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments, analytical instruments and laboratory middleware.

The term 'post-analytical instrument' as used herein can encompass any apparatus or apparatus component that can be configured to perform one or more post-analytical processing steps/workflow steps comprising—but not limited to—sample unloading, transport, recapping, decapping, temporary storage/buffering, archiving (refrigerated or not), retrieval and/or disposal.

The term 'pre-analytical instrument' as used herein can encompass any apparatus or apparatus component that can be configured to perform one or more pre-analytical processing steps/workflow steps comprising—but not limited to—centrifugation, resuspension (e.g., by mixing or vortexing), capping, decapping, recapping, sorting, tube type identification, sample quality determination and/or aliquotation steps. The processing steps may also comprise adding chemicals or buffers to a sample, concentrating a sample, incubating a sample, and the like.

The term 'analyzer'/'analytical instrument' as used herein can encompass any apparatus or apparatus component configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer comprises, without limitation, can be concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent-holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'laboratory middleware' as used herein can refer to any physical or virtual processing device configurable to control a laboratory instrument or system comprising one or more laboratory instruments in a way that workflow(s) and workflow step(s) can be conducted by the laboratory instrument/system. The laboratory middleware may, for example, instruct the laboratory instrument/system to conduct pre-analytical, post analytical and analytical workflow(s)/workflow step(s). The laboratory middleware may receive information from a data management unit regarding which steps need to be performed with a certain sample. In some embodiments, the laboratory middleware can be integral with a data management unit, can be comprised by a server computer and/or be part of one laboratory instrument or even distributed across multiple instruments of the laboratory system. The laboratory middleware may, for instance, be embodied as a programmable logic controller running a computer-readable program provided with instructions to perform operations.

The term 'sample transportation system' as used herein can encompass any apparatus or apparatus component that can be configured to transport sample carriers (each holding one or more sample containers) between laboratory instruments. In particular, the sample transportation system can be a one-dimensional conveyor-belt based system, a two-dimensional transportation system (such as a magnetic sample carrier transport system) or a combination thereof.

A 'laboratory system' as used herein can comprise a system comprising one or more analytical; pre- and post-analytical laboratory instruments, a sample transportation system and/or a laboratory middleware.

The term 'analysis or 'analytical test' as used herein can encompass a laboratory procedure characterizing a parameter of a biological sample for qualitatively assessing or quantitatively measuring the presence or amount or the functional activity of an analyte.

The term 'consumable' can comprise—but is not limited—to reagents, system fluids, quality control material, calibrator materials, microplates/microwell plates, reaction vessels, measurement cuvettes, sample tubes, pipetting tips, and the like.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

The term 'remote system' or 'server' as used herein can encompass any physical machine or virtual machine having a physical or virtual processor, capable of receiving; processing and sending data. A server can run on any computer including dedicated computers, which individually can also often be referred to as 'the server' or shared resources such as virtual servers. In many cases, a computer can provide several services and have several servers running. Therefore, the term server may encompass any computerized device that shares a resource with one or more client processes. Furthermore, the terms 'remote system' or 'server' can encompass a data transmission and processing system distributed over a data network (such as a cloud environment).

The term 'user interface' as used herein can encompass any suitable piece of software and/or hardware for interactions between an operator and a machine, including but not limited to a graphical user interface (GUI) for receiving as input a command from an operator and also to provide feedback and convey information thereto. In addition, a system/device may expose several user interfaces to serve different kinds of users/operators.

The term 'quality control' or 'analytical quality control' can refer to all those processes and procedures designed to ensure that the results of laboratory analysis (analytical tests) can be consistent, comparable, accurate and within specified limits of precision.

Disclosed herein is a maintenance method for a laboratory system, wherein the laboratory system can comprise a first group and second group of laboratory instruments for processing biological samples, a plurality of data collection components communicatively connected to the first group or the second group of laboratory instruments and a remote maintenance system communicatively connected to the data collection components. The first group of laboratory instruments can be connected to a first data collection component while the second group of laboratory instruments can be connected to a second data collection component. The data collection components can be dedicated for a specific group of laboratory instruments and have direct access to operative data of the laboratory instruments. According to embodiments disclosed herein, one data collection component can be communicatively connected to each group of laboratory instruments.

The maintenance method for a laboratory system can comprise collecting operational data from the laboratory instruments by the data collection components. The operational data collected from the laboratory instruments can be indicative of one or more operational parameters of the respective laboratory instruments.

According to embodiments disclosed herein, operational data of laboratory instruments of the first group of laboratory instruments can be collected by the first of the plurality of data collection components and operational data of laboratory instruments of the second group of laboratory instruments can be collected by a second of the plurality of data collection components.

The maintenance method for a laboratory system can also comprise detecting an anomaly related to one or more of the plurality of laboratory instruments of the first group by the first of the plurality of data collection components. Optionally, in addition, an anomaly related to one or more of the plurality of laboratory instruments of the second group can be detected by the second of the plurality of data collection components.

According to embodiments disclosed herein, an anomaly can be indicative of a failure/suboptimal operation of a laboratory instrument/system reflected by a deviation of the operational parameter(s) from standard value(s) and/or ranges.

The maintenance method for a laboratory system can also comprise transmitting context data by the first of the plurality of data collection components to the remote maintenance system upon detection of an anomaly. The context data sent by the first of the plurality of data collection components to the remote maintenance system can comprise both the operational data and data indicative of the anomaly. Optionally, in addition, context data can be transmitted by the second of the plurality of data collection components to the remote maintenance system upon detection of an anomaly. The context data sent by the second of the plurality of data collection components to the remote maintenance system can comprise both the operational data and data indicative of the anomaly.

The maintenance method for a laboratory system can also comprise determining one or more correlation(s) between the operational data and the anomaly(s) at the remote maintenance system.

According to embodiments disclosed herein, a correlation can be indicative of an (repeated) occurrence of an anomaly associated with particular operational data (such as within a certain time period).

According to embodiments disclosed herein, correlation(s) between the operational data and the anomaly(s) can be determined by receiving input (e.g., from an expert) indicative of such correlation(s). Alternatively, or additionally, correlation(s) between the operational data and the anomaly(s) can be determined automatically using pattern recognition methods such as, for example, based on preceding determination(s) by an expert.

According to embodiments disclosed herein, correlation(s) between operational data transmitted by the first of the plurality of data collection components and the anomaly(s) can be determined and/or correlation(s) between operational data transmitted by the second of the plurality of collection components and the anomaly(s) are determined.

The maintenance method for a laboratory system can also comprise validating one or more correlation(s) and marking the respective correlations as validated. Since correlation may not always be indicative of causality, the correlation(s) between the operational data and the anomaly(s) may need to be validated. A validated correlation can be an indication of a (probable) causality between particular operational data and an anomaly.

According to embodiments disclosed herein, the correlation(s) between the operational data and the anomaly(s) can be validated by receiving input (e.g., from an expert) indicative of a validity (probable causality) of the correlation(s) between the operational data and the anomaly(s). Alternatively, or additionally, the correlation(s) between the operational data and the anomaly(s) can be validated by instructing a computer implemented validation engine to validate the correlation(s) between the operational data and the anomaly(s) such as, for example, based on preceding validation(s) by an expert.

According to some embodiments, the correlation(s) between the operational data transmitted by the first of the plurality of data collection components and the anomaly(s) can be validated by comparing them with validated correlations of operational data transmitted by the second of the plurality of data collection components and the anomaly(s). Thus, validated correlations derived from operational data transmitted by the second of the plurality of data collection components may be used as a references for validating correlation(s) between the operational data transmitted by the first of the plurality of data collection components and the anomaly(s).

The maintenance method for a laboratory system can also comprise determining at the remote maintenance system one or more predictive rules corresponding to validated correlations.

According to embodiments disclosed herein, a predictive rule can comprise a condition, which, if met by the operational data, can predict the occurrence of the anomaly with a certain probability in a certain amount of timeframe and/or dependent on a further predictive rule (nested or dependent rule).

In order to allow the data collection components to timely predict the occurrence of an anomaly, the one or more predictive rule(s) can be transmitted by the remote maintenance system to the data collection components.

According to embodiments disclosed herein, the predictive rule(s) can be transmitted by the remote maintenance system also to data collection components, which (for data privacy or other reasons) do not themselves transmit context data to the remote maintenance system.

The maintenance method for a laboratory system can also comprise predicting occurrence of an anomaly of one or more of the plurality of laboratory instruments based on the one or more predictive rule(s) by one or more of the plurality of data collection components. According to embodiments disclosed herein, the data collection components can predict the anomaly(s) with a certain rate of probability.

Embodiments disclosed herein can be advantageous as they combine the advantages associated with direct access to operational data of the instruments to detect and predict anomalies with leveraging the power of centralized processing of operational data by the remote maintenance system.

By performing the data collection and anomaly detection locally by the data collection components, embodiments disclosed herein can ensure that the detection of anomalies can be based on all data available locally (within the respective group of instruments—without limitations due to volume and/or privacy) and without delays due to transmission to a remote location. This can allow a more precise detection of anomalies and ensure that the most relevant operational data can be associated with the anomaly.

By transmitting operational data associated with the anomaly to the remote maintenance system and performing the data analytics (determination and validation of correlations as well as determination of predictive rules) at a centralized location, embodiments disclosed herein can combine the data from multiple groups of laboratory instruments in order to collaboratively harvest and centrally analyze as much of the available data as possible.

By transmitting the one or more predictive rule(s) to the data collection components and predicting anomalies by the data collection components, embodiments disclosed herein can allow a much more timely prediction of anomalies by avoiding possible lags due to transmission of data to a remote location. Furthermore, predicting anomalies by the data collection components can ensure that the prediction of anomalies can be based on the entire operative data available locally within the respective group of instruments.

According to further embodiments disclosed herein, the maintenance method can further comprise determining at the remote maintenance system one or more prescriptive maintenance action(s) corresponding to the anomaly, transmitting the one or more prescriptive maintenance action(s) from the remote maintenance system to the plurality of data collection components and one or more of the plurality of collection components instructing one or more of the laboratory instruments to execute the one or more prescriptive maintenance action(s) upon predicting occurrence of an anomaly related thereto. The one or more prescriptive maintenance action(s) can comprise instruction(s) which, when executed by one or more of the laboratory instruments, can reduce the probability of occurrence of the anomaly.

In order to address cases when—despite predictive rules being used to predict anomalies—an anomaly nevertheless occurs, further embodiments disclosed herein can comprise determining anomaly mitigation action(s) corresponding to the anomaly; transmitting the mitigation action(s) from the remote maintenance system to the plurality of data collection components; and the data collection component instructing laboratory instrument(s) to execute anomaly mitigation action(s) if the anomaly has been detected by the data collection component which instructed one or more of the laboratory instruments to execute the one or more prescriptive maintenance action(s). The one or more anomaly mitigation action(s) can comprise instruction(s) which, when executed by one or more of the laboratory instruments, can mitigate the negative effects of the anomaly. In other words, the impact of the anomaly can be reduced.

Further embodiments disclosed herein can relate to a maintenance method wherein the remote maintenance system can comprise one or more regional server(s) each communicatively connected to a plurality of data collection components. The method can further comprise the step of each regional server analyzing operational parameters common to all and/or common to a subset of laboratory instruments connected to the particular regional server in order to detect correlation(s) between operational data and anomaly(s) specific to the respective region. Such embodiments can be advantageous as they can allow a compromise between use of a data set as large as possible for advanced analytics and the amount/type of data transmitted between different regions—thereby fulfilling limitations due to data privacy regulations.

Overall, embodiments disclosed herein effectively can combine edge computing for comprehensive and timely data capture respectively anomaly prediction (avoiding data volume and/or privacy limitations) with the power of cloud computing for advanced data analysis based on multiple data sources as well as quality assurance by validations.

Referring initially to FIG. 1, the disclosed laboratory system 100 can comprise a plurality of laboratory instruments 10 grouped into a first group 1 and second group 2 of laboratory instruments 10. The laboratory instruments 10 can be communicatively connected (e.g., by a communication network) to one of the plurality of data collection components 20.1, 20.2. In the example shown on FIG. 1, the first group 1 of laboratory instruments 10 can be connected to a first data collection component 20.1 while the second group 2 of laboratory instruments 10 can be connected to a second data collection component 20.2. In the example of FIG. 1, an optional laboratory middleware 15 is illustrated, which can be configured to instruct a plurality of laboratory instruments 10 to process biological samples according to one or more test orders. According to various embodiments disclosed herein, the data collection components 20.1, 20.2 can be connected to the laboratory instruments 10 either directly or via laboratory middleware 15. It can be noted that the data collection components 20.1, 20.2 can either be dedicated hardware units and/or part of a server computer such as the laboratory middleware 15, a router, or any computing device configured to carry out the functions of the data collection components as disclosed herein (e.g., in a server instance/process and/or a virtual machine). Common to the data collection components 20.1, 20.2 of all embodiments can be that they can be dedicated for a specific group of laboratory instruments 10 and have direct access to operative data of the laboratory instruments 10.

The data collection components 20.1, 20.2 can be communicatively connected to the remote maintenance system 50, e.g., by a communication network. The term remote with respect to a remote maintenance system can be understood as a computer system located at a location different from at least one of the first or second group of laboratory instruments 10.

Figure 2:
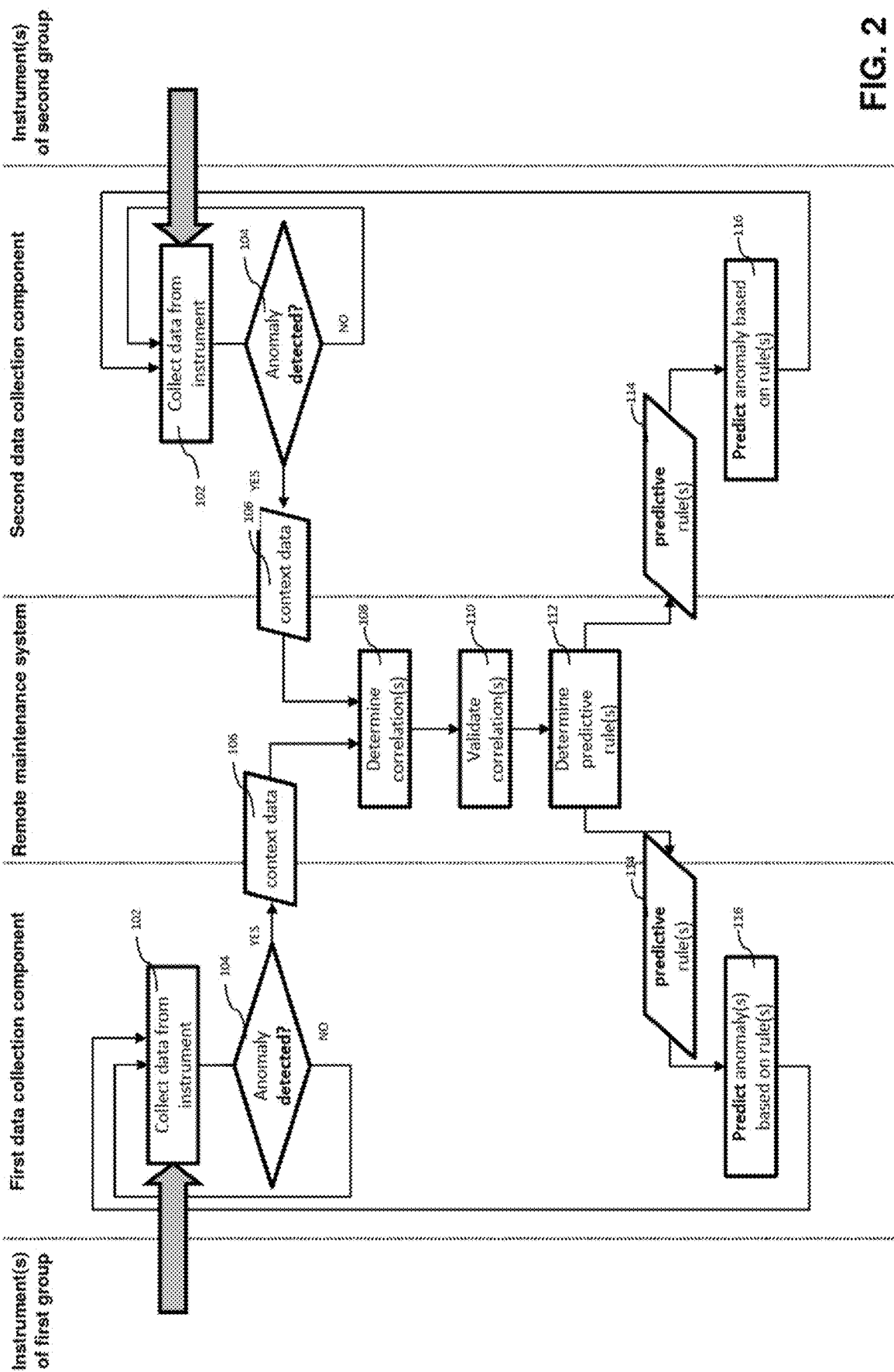
FIG. 2 illustrates a swim-lane diagram showing the interaction between elements of the system carrying out a first embodiment of the disclosed method according to an embodiment of the present disclosure.
Figure 3A:
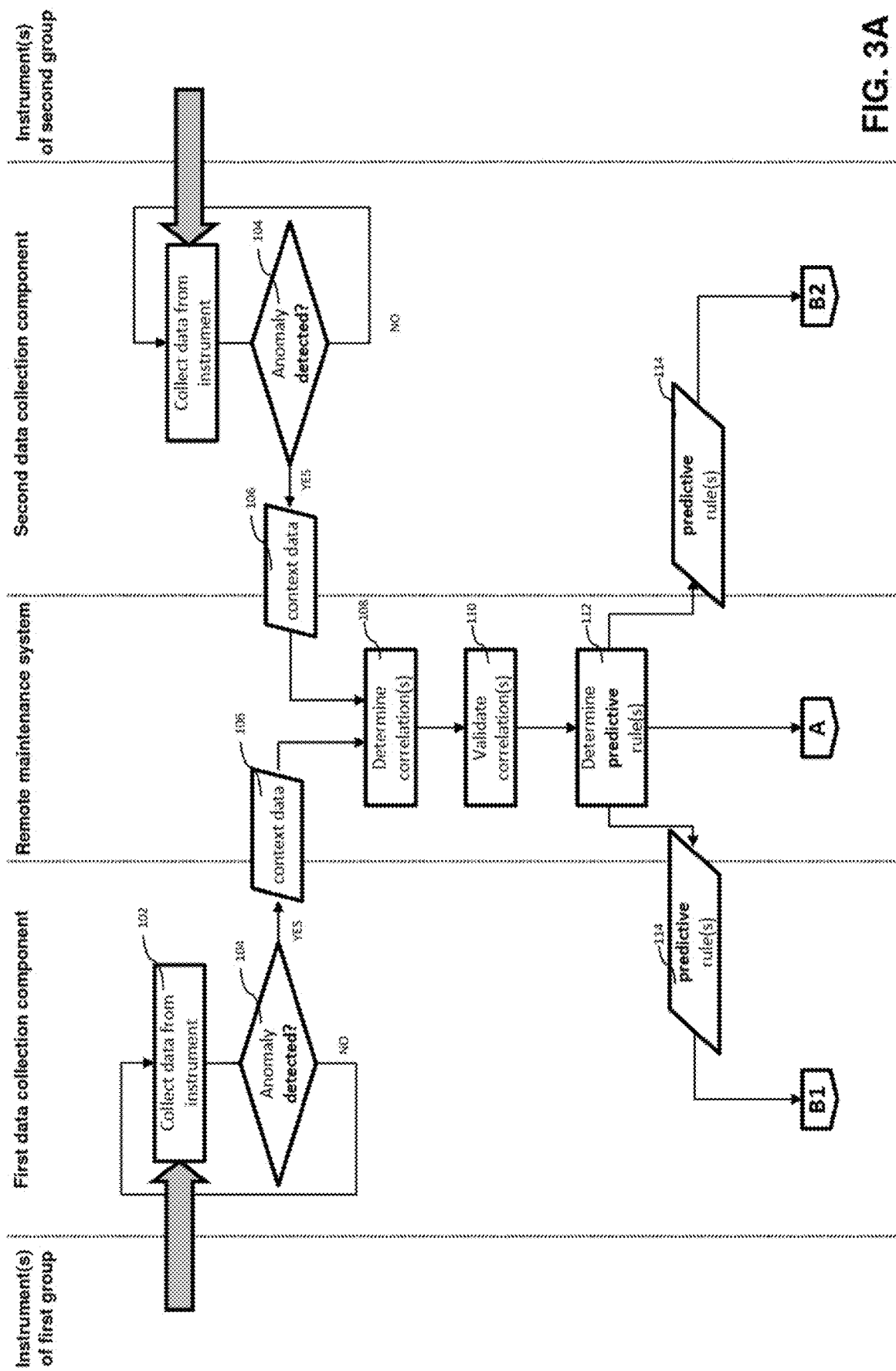
FIG. 3A illustrates a first page of a swim-lane diagram showing the interaction between elements of the system carrying out a further embodiment of the disclosed method according to an embodiment of the present disclosure.
Figure 3B:
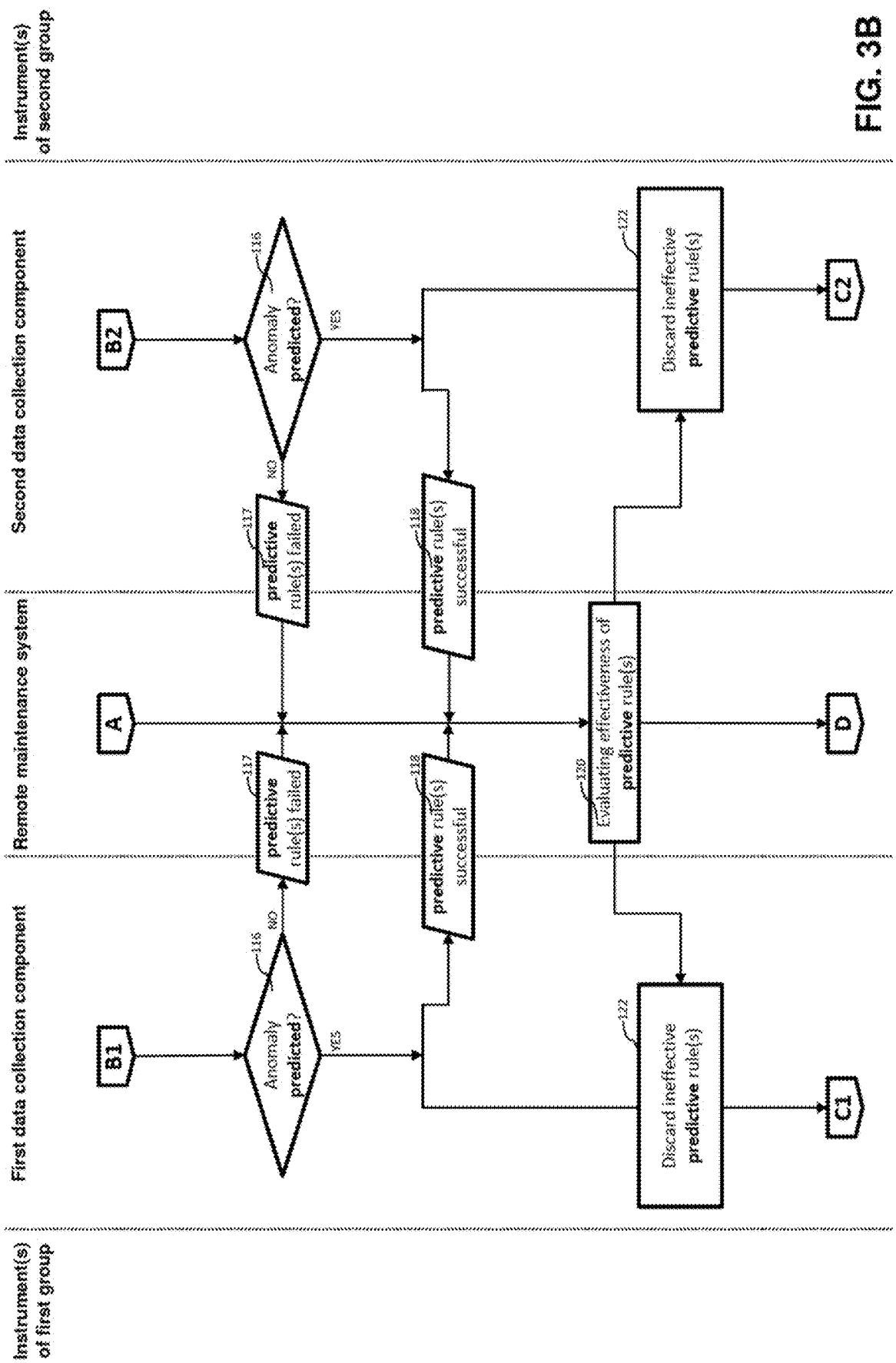
FIG. 3B illustrates a second page of a swim-lane diagram showing the interaction between elements of the system carrying out a further embodiment of the disclosed method according to an embodiment of the present disclosure.
Figure 3C:
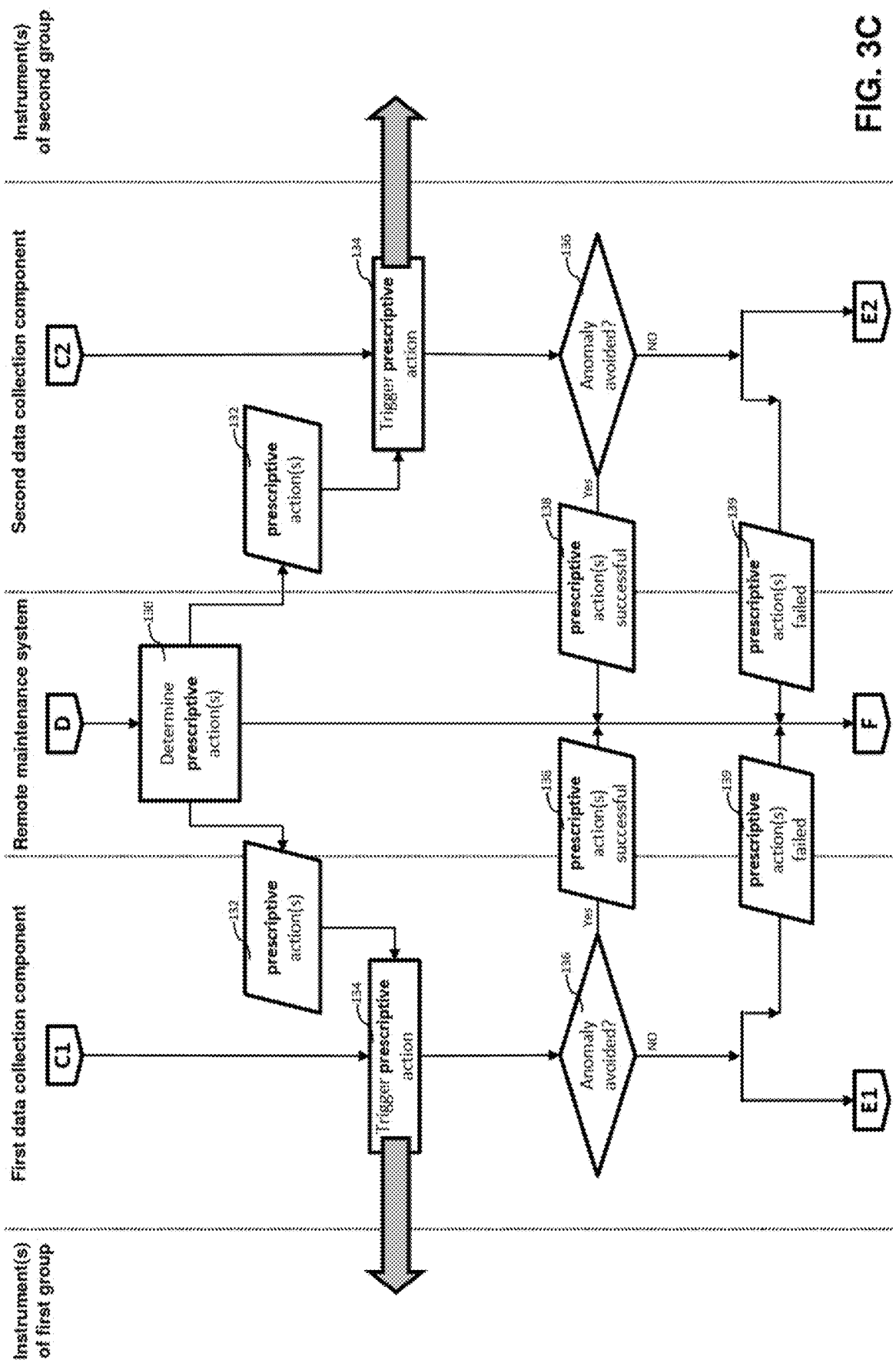
FIG. 3C illustrates a third page of a swim-lane diagram showing the interaction between elements of the system carrying out a further embodiment of the disclosed method further comprising prescriptive maintenance according to an embodiment of the present disclosure.
Figure 3D:
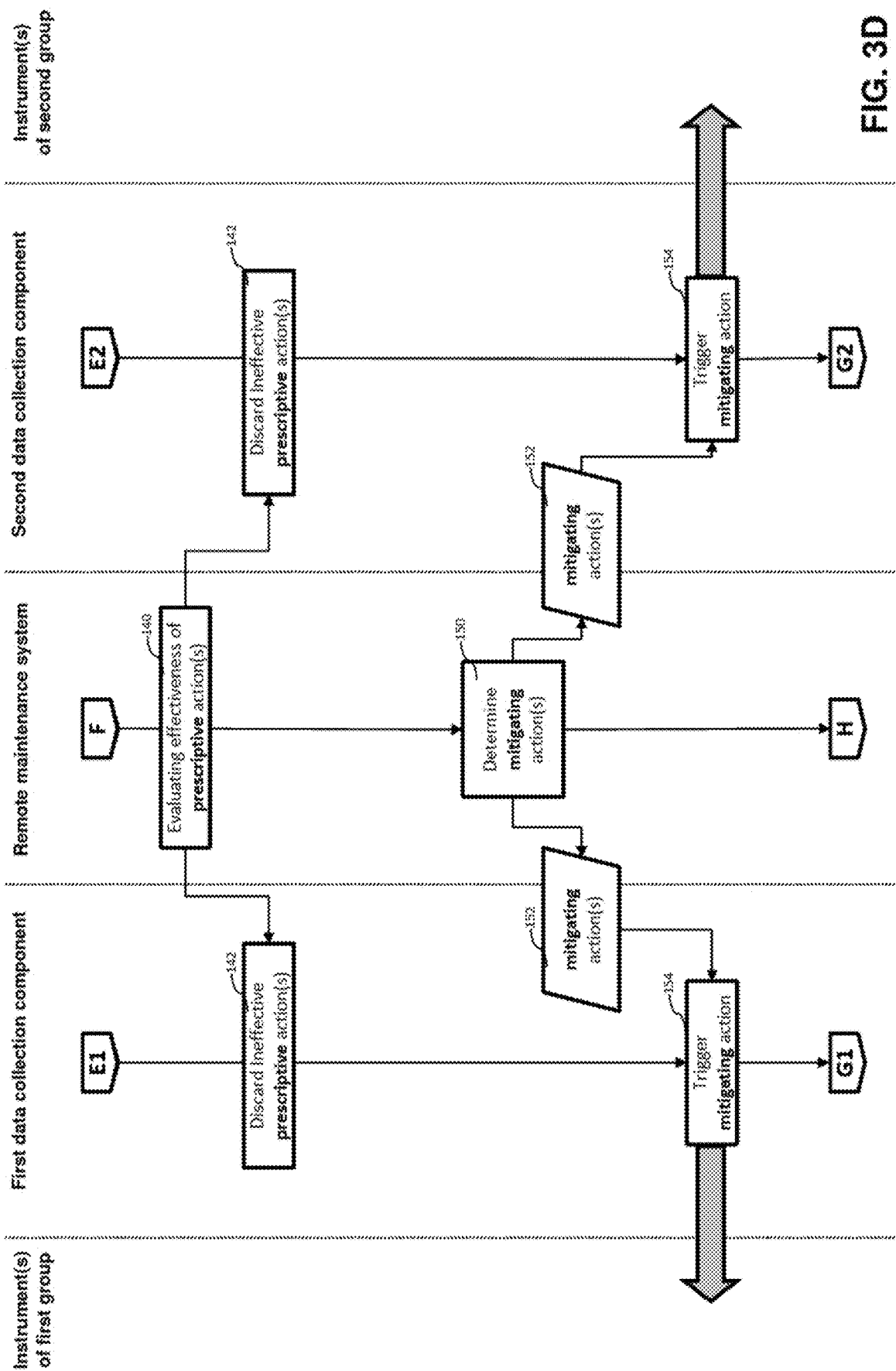
FIG. 3D illustrates a fourth page of a swim-lane diagram showing the interaction between elements of the system carrying out a further embodiment of the disclosed method further comprising mitigating actions according to an embodiment of the present disclosure.
Figure 3E:
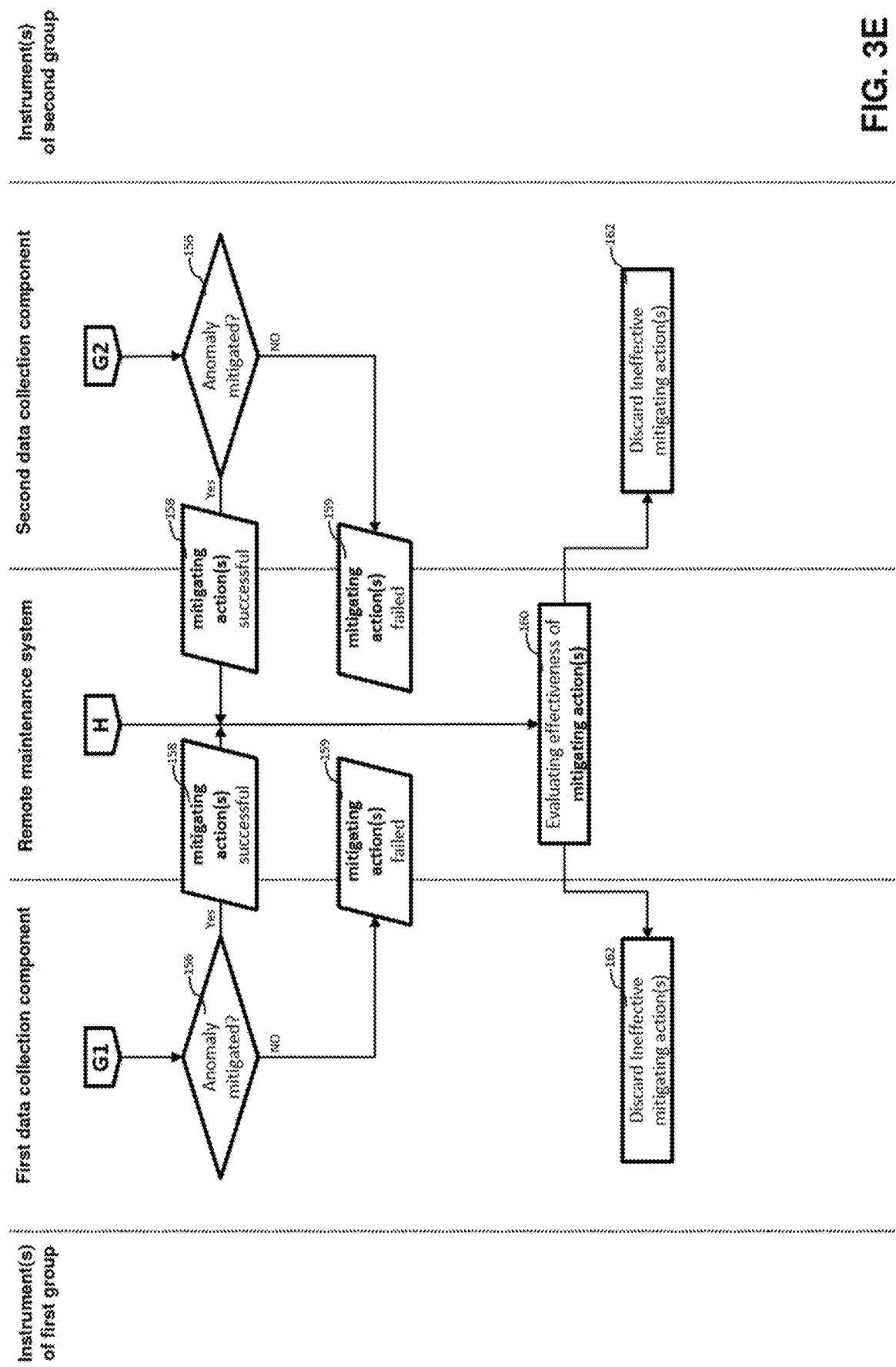
FIG. 3E illustrates a fifth page of a swim-lane diagram showing the interaction between elements of the system carrying out a further embodiment of the disclosed method further comprising evaluation of mitigating actions according to an embodiment of the present disclosure.

Turning now to FIGS. 2-3E, embodiments of the disclosed method will be described.

In a preparatory step, not explicitly shown in the figures, laboratory instruments can be grouped into various groups. The grouping of laboratory instruments may be based on a common physical location of the respective laboratory instruments and/or a logical grouping by the type, manufacturer and/or work area of the respective laboratory instruments. According to embodiments disclosed herein, laboratory instruments of a particular group may even be located at different physical locations.

In a further preparatory step, each group of laboratory instruments can be communicatively connected to a data collection component, e.g., by a communication network.

FIG. 2 shows a swim-lane diagram showing the interaction between elements of the system carrying out a first embodiment of the disclosed method.

In a first step 102, the data collection components 20.1, 20.2 can collect operational data from the laboratory instruments 10 of the first group or the second group 2. The operational data can be indicative of one or more operational parameters of the respective laboratory instruments 10.

According to embodiments disclosed herein, the operational data can comprise one or more of:

Environmental factors like humidity, temperature, air, water, power supply quality, vibration provided by sensors within the respective laboratory instrument, indicative of a condition of one or more components of the laboratory instrument, such as temperature, humidity, voltage, current, torque (e.g., of a motor), noise and/or vibrations and provided by sensors arranged outside the laboratory instruments, providing data indicative of temperature, humidity, voltage, current, torque (e.g., of a motor), noise and/or vibrations in the proximity of the laboratory instruments;

Operational factors such as throughput, quality control (QC) and calibration frequency of the laboratory instruments;

Device performance factors like QC and calibration results, error messages, log files of the laboratory instruments;

Data on consumables comprising expiration date, transport and storage conditions;

Data on operator handling comprising performance/non-performance of maintenance activities, customer maintenance due/overdue;

Data indicative of hardware (HW) and software (SW) performance comprising availability/non-availability of storage space and/or memory, up-to-dateness of software.

According to embodiments disclosed herein, the operational factors, the data on consumables, data on operator handling and/or data indicative of HW and SW performance can be retrieved by the data collection components from the laboratory instruments and/or determined by the data collection components based on data from the laboratory instruments.

In a subsequent step 104, anomalies related to one or more of the plurality of laboratory instruments 10 of the first group 1 can be detected by the first of the plurality of data collection components 20.1.

According to embodiments disclosed herein, the data collection components 20.1, 20.2 can detect anomalies by applying one or more anomaly detection rules, comprising detecting deviations of the operational parameters from set threshold values. The threshold values can be set either by a manufacturer of the respective laboratory instruments and/or set by an operator of the laboratory system. In particular, the step 104 of detecting an anomaly related to one or more of the plurality of laboratory instruments 10 can comprise: detecting deviation(s) of one or more operating parameters of the laboratory instrument 10 from manufacturer's operational ranges and/or detecting deviation(s) of one or more environmental parameters around the laboratory instrument 10 based on data captured by one or more sensors located in the proximity of but outside the laboratory instrument 10 and communicatively connected to one of the plurality of data collection components 20.1, 20.2.

Additionally, or alternatively, the data collection components 20.1, 20.2 can detect anomalies by consulting log file(s) of the laboratory instruments to identify log entries that could point to an anomaly related to the respective laboratory instrument(s).

Thus, the data collection components 20.1, 20.2 can detect anomalies based on the collected operational data, e.g., operational parameters, environmental data, and/or log file entries. For example, the data collection components 20.1, 20.2 can detect anomalies of one or more of the plurality of laboratory instruments 10 by detecting deviations of one or more operational parameters from set threshold values, by detecting deviations of one or more environmental parameters from set threshold values, and/or by identifying log entries that could point to an anomaly.

Data indicative of an anomaly can comprise any data indicative of an anomaly, e.g., deviations of operational data and/or an indication that an anomaly has occurred and to which type of anomaly has occurred (e.g., as a flag in a log file). The data indicative of an anomaly can be created automatically and/or by input (e.g., from an expert).

The data collection components 20.1, 20.2 can e.g., detect anomalies of one or more of the plurality of laboratory instruments 10 by detecting a failure of a laboratory instrument/system or system components and/or a deviation of the respective instrument from a status considered as normal respectively accepted operation. The normal respectively accepted operation can be e.g., defined by one or more of: operating parameters/specification defined by the manufacturer/owner/regulatory body, statistically determined mean/average values of the respective operating parameters of identical or similar instruments (peer comparison), and/or operation marked by an operator/technician/expert as normal operation.

According to embodiments disclosed herein, in step 104, anomalies related to one or more of the plurality of laboratory instruments 10 of the first group 1 can be detected by the first of the plurality of data collection components 20.1 and/or anomalies related to one or more of the plurality of laboratory instruments 10 of the second group 2 can be detected by the second of the plurality of data collection components 20.2.

Upon detection of an anomaly, in a step 106, the first of the plurality of data collection components 20.1 can transmit context data to the remote maintenance system 50. The term 'upon' can be understood to comprise transmission immediately (as technically feasible) after the detection of the anomaly and/or transmission after the detection of the anomaly based on a schedule and/or transmission as soon as a network connection between the first data collection component 20.1 to the remote maintenance system 50 for such transmission becomes available. The context data can comprise both operational data and data indicative of the anomaly. According to embodiments disclosed herein, the context data can comprise only operational data related to the anomaly, such as operational data collected during and a specified amount of time before and/or after the anomaly has been detected. Furthermore, operational data related to the anomaly may comprise test result data of the respective laboratory instruments generated during and/or a specified amount of time before and/or after the anomaly has been detected.

According to embodiments disclosed herein, upon detection of an anomaly, in step 106, the first of the plurality of data collection components 20.1 can transmit context data to the remote maintenance system 50 and/or the second of the plurality of data collection components 20.2 can transmit context data to the remote maintenance system 50.

According to embodiments disclosed herein, the plurality of data collection components 20.1, 20.2 can filter out sensitive data from the operational data collected from the plurality of laboratory instruments 10, before transmitting the operational data to the remote maintenance system 50. For example, sensitive data can comprise data identifying a patient, results of analytical tests performed by one of the laboratory instruments and/or any data that can be classified as sensitive in view of regulations or rules set by an operator of the laboratory system 100.

Based on the context data transmitted by data collection components 20.1, 20.2, in a step 108, one or more correlation(s) between the operational data and the anomaly(s) can be determined at the remote maintenance system 50. According to embodiments disclosed herein, correlation(s) between the operational data and the anomaly(s) can be determined by receiving input (e.g., from an expert) indicative of such correlation(s). Alternatively, or additionally, correlation(s) between the operational data and the anomaly(s) can be determined automatically using a set of rules, pattern recognition methods such as, for example, based on preceding determination(s) by an expert (expert supervised pattern matching). According to further embodiments disclosed herein, machine-learning methods can be employed in order to improve the detection of correlations, having preceding expert determined correlations as teaching data.

However, since a correlation is not necessarily associated with a causal relationship, in a step 110, correlations can be validated at the remote maintenance system 50. A validated correlation is an indication of a (probable) causality between particular operational data and an anomaly. According to various embodiments disclosed herein, a degree/percentage of probability of a causality can be set above which a correlation can be validated. According to embodiments disclosed herein, the degree/percentage of probability (of a causality above which a correlation is validated) can be set at different levels corresponding to different anomalies or types of anomalies, for example by the severity/impact of the respective anomaly. According to embodiments disclosed herein, correlation(s) between the operational data and the anomaly(s) can be validated by receiving input (e.g., from an expert) indicative of such validation(s). Alternatively, or additionally, correlation(s) between the operational data and the anomaly(s) can be validated automatically using a set of rules, pattern recognition methods such as, for example, based on preceding validation(s) by an expert (expert supervised pattern matching). According to further embodiments disclosed herein, machine-learning methods can be employed in order to improve the validation of correlations, having preceding expert determined validations as teaching data.

The following example can further exemplify steps 102 to 110: An analytical instrument can comprise multiple components (e.g., pipetting device, heating device, light source, detection device) and each component can obtain measurement values such as quality control (QC) results. A data collection component 20.1, 20.2 can collect operational data comprising the QC results and operational data of each component. The operational data of each of the components can be provided by sensors within the analytical instrument and can be indicative of a condition of the component of the analytical instrument. The data collection component can detect an anomaly by detecting a deviation of the QC results from a predefined range or target value. Upon detection of the deviation of the QC results, the data collection component can transmit context data comprising the deviation of the QC results (data indicative of the anomaly) and the operational data of each component to the remote maintenance system 50. The transmitted context data can comprise only operational data of the components related to the anomaly, e.g., operational data of each component collected during a specified amount of time before and/or after the deviation of the QC results has been detected. Subsequently, the remote maintenance system 50 can determine one or more correlation(s) between the operational data of the components and the deviation of the QC results. Operational data of some components may correlate with the deviation of the QC results whereas operational data of other components may not correlate with the deviation of the QC results. For example, operational data of the heating device and the light source can correlate with the deviation of QC results, whereas operational data of the pipetting device and detection device do not correlate with the deviation of QC results. Then, the determined correlations of the operational data of the heating device and the light source can be validated in order to determine a causality between the determined correlation(s) of the operational data of the corresponding components and the deviation of QC results. For example, only the condition of the light source may be relevant and can have an impact on the measurement of QC results, whereas the condition of the heating device may not be relevant. Accordingly, only the correlation of the operational data of the light source and the deviation of the QC result can be validated. Thus, based on the determination of correlations and subsequent validation of the determined correlations the causality of a condition of one or more of the multiple components and an anomaly can be determined.

According to embodiments disclosed herein, the plurality of data collection components 20.1, 20.2 can filter out some of the operational data collected from the plurality of laboratory instruments 10, before transmitting the operational data to the remote maintenance system 50. For example, the plurality of data collection components 20.1, 20.2 can filter out operational data for which correlations were not validated, i.e., rejected, in preceding validations. Accordingly, by filtering out operational data, which would lead to invalid correlations, the transmitted data volume to the remote maintenance system 50 can be further reduced.

In a subsequent step 112, one or more predictive rules can be determined corresponding to validated correlations at the remote maintenance system 50. A predictive rule can comprise a condition, which, if met by operational data, can predict the occurrence of the anomaly with a certain probability in a certain amount of timeframe. According to embodiments disclosed herein, the probability and timeframe of occurrence of the anomaly can be set at different levels corresponding to different anomalies or types of anomalies, for example by the severity/impact of the respective anomaly. According to embodiments disclosed herein, the probability of occurrence of the anomaly defined by the predictive rules(s) can be equal to the probability of a causality. According to further embodiments disclosed herein, the probability of occurrence of the anomaly defined by the predictive rules(s) can be determined as a function of the probability of a causality, for example, the probability of a causality may be multiplied by a value specific to a particular group of laboratory instruments, such as an anomaly risk factor.

According to embodiments disclosed herein, predictive rules(s) can be determined by receiving input (e.g., from an expert) indicative of such predictive rules(s). Alternatively, or additionally, predictive rules(s) can be determined automatically using a set of rules, pattern recognition methods such as, for example, based on preceding predictive rules(s) determined by an expert (expert supervised pattern matching). According to further embodiments disclosed herein, machine-learning methods can be employed in order to improve the determination of predictive rule(s), having preceding expert determined predictive rules as teaching data.

In a subsequent step 114, the one or more predictive rule(s) can be transmitted by the remote maintenance system 50 to the data collection components 20.1, 20.2. The predictive rules can be transmitted either immediately (as technically feasible) after their determination and/or based on a distribution schedule and/or as soon as a network connection between the remote maintenance system 50 and the data collection components 20.1, 20.2 becomes available.

According to embodiments disclosed herein, the one or more predictive rule(s) can be transmitted by the remote maintenance system 50 to the first of the plurality of data collection components 20.1 and/or to the second of the plurality of data collection components, 20.2.

Having received one or more predictive rule(s), in a step 116, the one or more of the plurality of data collection components 20.1, 20.2 can predict occurrence of anomaly(s) of one or more of the plurality of laboratory instruments 10 based on the one or more predictive rule(s). The step 116 of predicting an occurrence of an anomaly(s) can comprise determining with a defined probability that the respective anomaly is about to occur in a certain amount of time.

By deploying the predictive rules to the data collection components 20.1, 20.2, the disclosed method/system can allow timely prediction of the occurrence of an anomaly. Furthermore, by deploying the predictive rules to the data collection components 20.1, 20.2, the disclosed method/system can allow prediction of anomalies also with respect to laboratory instruments 10, the context data of which may not be available (or restricted) at the remote maintenance server 50—for privacy or technical reasons. This can offer a significant advantage over known solutions by allowing anomaly prediction even for laboratory instruments 10 which themselves may not upload data to a remote location. According to particular embodiments disclosed herein, the predictive rules may even be distributed to certain data collection components on offline data carriers such as a portable storage device, an optical or magnetic data carrier.

According to embodiments disclosed herein, upon predicting occurrence of an anomaly, the frequency and/or volume and/or selection of parameters of the operational data from the laboratory instruments 10 captured by the data collection components 20.1, 20.2 can be increased or changed. In other words, upon predicting occurrence of an anomaly, the data collection components 20.1, 20.2 can monitor the laboratory instruments 10 much more closely, in particular, for a set period of close monitoring.

Turning now to FIGS. 3A-E further embodiments of the disclosed method will be described.

FIG. 3A shows a first page of a swim-lane diagram until off page connectors A, B1 and B2. FIG. 3B shows the second page of the swim-lane diagram of FIGS. 3A-E, as from the off-page connectors A, B1 and B2.

According to further embodiments disclosed herein, as shown on FIG. 3B, if in step 116 an anomaly has been detected but not predicted, in step 117, the respective data collection component 20.1, 20.2 can transmit data indicative of failure of the one or more predictive rule(s) to the remote maintenance system 50 such as, for example, failure of the predictive rules associated with the detected but unpredicted anomaly. On the other hand, if the anomaly has been predicted by a data collection component 20.1, 20.2 using a predictive rule, in a step 118, the respective data collection component 20.1, 20.2 can transmit data indicative of success of the predictive rule(s) that predicted the anomaly. According to particular embodiments, the success of the predictive rules can be confirmed before transmitting data indicative of its success in order to rule out false positives. The confirmation of success may be performed either by receiving input (from an expert) indicative of success of the predictive rule and/or determined automatically using a set of rules, pattern recognition methods such as, for example, based on preceding confirmations by an expert (expert supervised pattern matching). According to further embodiments disclosed herein, machine-learning methods can be employed in order to improve the confirmation of predictive rules, having preceding expert confirmations as teaching data.

In a subsequent step 120, the remote maintenance system 50 can evaluates data indicative of the success or the failure of predictive rule(s). Predictive rule(s) can be flagged as effective if the data indicative of the success outweighs data indicative of the failure. On the other hand, predictive rule(s) can be flagged as ineffective if the data indicative of the failure outweighs data indicative of the success. The term outweighs can be understood to comprise a comparison of the number of indications of the success versus the failure. Alternatively, or additionally, a weighted function may be applied wherein data indicative of the failure can be considered with a different weight as compared to data indicative of the success. Furthermore, the source of such indications (the particular data collection component) may affect the weighting of the indication of the success or the failure. Following the evaluation of step 120, the remote maintenance system 50 can instruct the plurality of data collection components 20.1, 20.2 to discard predictive rule(s) flagged as ineffective. Discarding can be understood to comprise deletion from the list of stored predictive rules and/or deactivating the predictive rules and/or flagging for review (by an expert) any prediction resulting from a predictive rule marked as ineffective.

FIG. 3C shows the third page of the swim-lane diagram of FIGS. 3A-E, as from the off-page connectors C1, C2 and D of FIG. 3B.

According to embodiments disclosed herein and illustrated on FIG. 3C, in a step 130, one or more prescriptive maintenance action(s) corresponding to the anomaly can be determined at the remote maintenance system 50. A prescriptive maintenance action can comprise instruction(s), which, when executed with respect to one or more of the laboratory instruments 10, can reduce the probability of occurrence of the anomaly. According to embodiments disclosed herein, prescriptive maintenance action(s) can be determined by receiving input (e.g., from an expert) indicative of such prescriptive maintenance action(s). Alternatively, or additionally, maintenance action(s) can be determined automatically using a set of rules, pattern recognition methods such as, for example, based on preceding prescriptive maintenance action(s) determined by an expert (expert supervised pattern matching). According to further embodiments disclosed herein, machine-learning methods can be employed in order to improve the determination of maintenance action(s), having preceding expert determined maintenance action as teaching data.

In a subsequent step 132, the one or more prescriptive maintenance action(s) can be transmitted from the remote maintenance system 50 to the plurality of data collection components 20.1, 20.2.

Upon predicting occurrence of an anomaly, in a step 134, the one or more of the plurality of data collection components 20.1, 20.2 can trigger execution of the one or more prescriptive maintenance action(s).

According to embodiments disclosed herein, the prescriptive maintenance action can comprise computer readable instruction(s), the data collection components 20.1, 20.2 instructing the respective laboratory instruments 10 to execute the one or more prescriptive maintenance action(s). According to further embodiments disclosed herein, the prescriptive maintenance action can comprise human readable instruction(s) to be executed by an operator/service technician on laboratory instruments 10.

According to embodiments disclosed herein, the prescriptive maintenance action(s) can comprise one or more of the following:
  Updating a software or software component on the respective laboratory instrument 10.
  Causing a redistribution of a workload between a plurality of laboratory instruments 10. According to embodiments disclosed herein, redistribution of a workload between a plurality of laboratory instruments 10 can comprise instructing a laboratory middleware 15 to adjust one or more load balancing rules to reduce the load on the affected instrument.
  Redirecting of one or more biological samples from the laboratory instrument(s) 10 corresponding to the predicted anomaly to laboratory instrument(s) 10 other than the laboratory instrument(s) 10 corresponding to the predicted anomaly.
  Triggering replacement and/or service of one or more parts of the laboratory instrument(s) 10 corresponding to the predicted anomaly;
  Triggering calibration and/or quality control processes of the of the laboratory instrument(s) 10 corresponding to the predicted anomaly;
  Triggering the discarding of reagents and/or lots of reagents with a corresponding indication of improper handling and/or manufacturer recall;
  Triggering the discarding of laboratory instrument(s) 10 with a corresponding indication of improper maintenance.
  Triggering the automatic readjustment of laboratory instrument(s) or component(s) of the of laboratory instrument(s)

Triggering of prescriptive maintenance action(s) can comprise the data collection components 20.1, 20.2 instructing the respective laboratory instruments 10 to execute the one or more prescriptive maintenance action(s) and/or causing the prescriptive maintenance action to be provided as human readable instruction(s) to an operator/service technician to be executed. The human readable instruction(s) of the prescriptive maintenance action may be presented to the operator/service technician on user interface comprised by or connected to the respective laboratory instruments 10 and/or sent to the operator/service technician by electronic communication means, such as an email, SMS, instant messaging alert. Additionally, or alternatively, the human readable instruction(s) can be presented to the operator/service technician on a wearable device such as, for example, an augmented reality device configured to present the prescriptive maintenance action(s) as a series of steps to be carried out on the laboratory instrument 10.

In order to measure the effectiveness of the prescriptive maintenance actions, in a step 136, the data collection component 20.1, 20.2 that triggered execution of the one or more prescriptive maintenance action(s) can monitor the respective laboratory instrument 10 to determine whether the anomaly has been avoided. If the anomaly could not be detected, in a step 138, the data collection component 20.1, 20.2 can transmit data indicative of success of the prescriptive maintenance action(s) to the remote maintenance system 50. If—despite triggering of the prescriptive maintenance actions, the anomaly has been detected, in a step 139, the data collection component 20.1, 20.2 can transmit data indicative of failure of the prescriptive maintenance action(s).

FIG. 3D shows the fourth page of a swim-lane diagram from off-page connectors E1, E2 and F of FIG. 3C. As illustrated on FIG. 3D, in a step 140, the remote maintenance system 50 can evaluate data indicative of the success or the failure of prescriptive maintenance actions. Prescriptive maintenance actions can be flagged as effective if the data indicative of the success outweighs data indicative of the failure. On the other hand, prescriptive maintenance actions can be flagged as ineffective if the data indicative of the failure outweighs data indicative of the success. The term outweighs can be understood to comprise a comparison of the number of indications of the success versus the failure. Alternatively, or additionally, a weighted function may be applied wherein data indicative of the failure can be considered with a different weight as compared to data indicative of the success. Furthermore, the source of such indications (the particular data collection component) may affect the weighting of the indication of the success or the failure. Following the evaluation of step 140, in a step 142, the remote maintenance system 50 can instruct the plurality of data collection components 20.1, 20.2 to discard prescriptive maintenance actions flagged as ineffective. Discarding can be understood to comprise deletion from the list of stored prescriptive maintenance actions and/or deactivating the prescriptive maintenance actions and/or flagging for review (by an expert) any prescriptive maintenance actions marked as ineffective.

As further shown on FIG. 3D, according to embodiments disclosed herein, in order to reduce the impact (negative effects) of an anomaly, mitigation actions can be determined and distributed. In other words, the anomaly mitigation actions can come into effect when despite all efforts (preventive, prescriptive or other forms of maintenance), the anomaly occurs or is expected to occur in a certain amount of time. For example, if it is unavoidable that a component of a laboratory instrument 10 will fail, the anomaly mitigation action can comprise unloading of all unprocessed biological samples from the respective laboratory instrument 10 and transferring them to other laboratory instruments or into storage until the failure is rectified. According to further embodiments disclosed herein, mitigation actions can be deployed to data collection components 20.1, 20.2 of groups of laboratory instruments 10 which have not yet experienced the anomaly, but determined by the remote maintenance system 50 to be at risk of facing the anomaly. The mitigation action may be for example in the form of triggering new or renewed training activities of operators of the laboratory instruments.

In a step 150, one or more anomaly mitigation action(s) can be determined at the remote maintenance system 50 corresponding to the anomaly. The one or more anomaly mitigation action(s) can comprise instruction(s) which, when executed by one or more of the laboratory instruments 10, can mitigate the negative effects of the anomaly. According to embodiments disclosed herein, anomaly mitigation action(s) can be determined by receiving input (e.g., from an expert) indicative of such anomaly mitigation action(s). Alternatively, or additionally, anomaly mitigation action(s) can be determined automatically using a set of rules, pattern recognition methods such as, for example, based on preceding anomaly mitigation actions determined by an expert (expert supervised pattern matching). According to further embodiments disclosed herein, machine-learning methods can be employed in order to improve the determination of anomaly mitigation action(s), having preceding expert determined anomaly mitigation actions as teaching data.

According to embodiments disclosed herein, the anomaly mitigation action can comprise computer readable instruction(s), the data collection components 20.1, 20.2 instructing the respective laboratory instruments 10 to execute the one or more anomaly mitigation action(s). According to further embodiments disclosed herein, the anomaly mitigation action can comprise human readable instruction(s) to be executed by an operator/service technician on laboratory instruments 10.

In a step 152, the remote maintenance system 50 can transmit the one or more mitigation action(s) to the plurality of data collection components 20.1, 20.2.

In a subsequent step 154, the data collection component 20.1, 20.2 can trigger execution of one or more anomaly mitigation action(s) if the anomaly has been detected by the data collection component 20.1, 20.2 which instructed one or more of the laboratory instruments 10 to execute the one or more prescriptive maintenance action(s). Triggering of anomaly mitigation action(s) can comprise the data collection components 20.1, 20.2 instructing the respective laboratory instruments 10 to execute the one or more anomaly mitigation action(s) and/or causing the anomaly mitigation action to be provided as human readable instruction(s) to an operator/service technician to be executed.

FIG. 3E shows the fourth page of a swim-lane diagram from off-page connectors G1, G2 and F of FIG. 3D. In order to measure the effectiveness of the anomaly mitigation actions, in a step 156, the data collection component 20.1, 20.2 which triggered execution of the one or more anomaly mitigation action(s) can monitor the respective laboratory instrument 10 to determine whether the impact of the anomaly has been mitigated (reduced). If the anomaly could be mitigated, in a step 158, the data collection component 20.1, 20.2 can transmit data indicative of success of the anomaly mitigation action(s) to the remote maintenance system 50. If—despite triggering of the anomaly mitigation actions, the anomaly has not been mitigated, in a step 159, the data collection component 20.1, 20.2 can transmit data indicative of failure of the anomaly mitigation action(s).

As illustrated on FIG. 3E, in a step 160, the remote maintenance system 50 can evaluate data indicative of the success or the failure of anomaly mitigation actions. Anomaly mitigation actions can be flagged as effective if the data indicative of the success outweighs data indicative of the failure. On the other hand, anomaly mitigation actions can be flagged as ineffective if the data indicative of the failure outweighs data indicative of the success. The term outweighs can be understood to comprise a comparison of the number of indications of the success versus the failure. Alternatively, or additionally, a weighted function may be applied wherein data indicative of the failure is considered with a different weight as compared to data indicative of the success. Furthermore, the source of such indications (the particular data collection component) may affect the weighting of the indication of the success or the failure. Following the evaluation of step 160, in a step 162, the remote maintenance system 50 can instruct the plurality of data collection components 20.1, 20.2 to discard anomaly mitigation actions flagged as ineffective. Discarding can be understood to comprise deletion from the list of stored anomaly mitigation actions and/or deactivating the anomaly mitigation actions and/or flagging for review by an expert any anomaly mitigation actions marked as ineffective.

Figure 4:
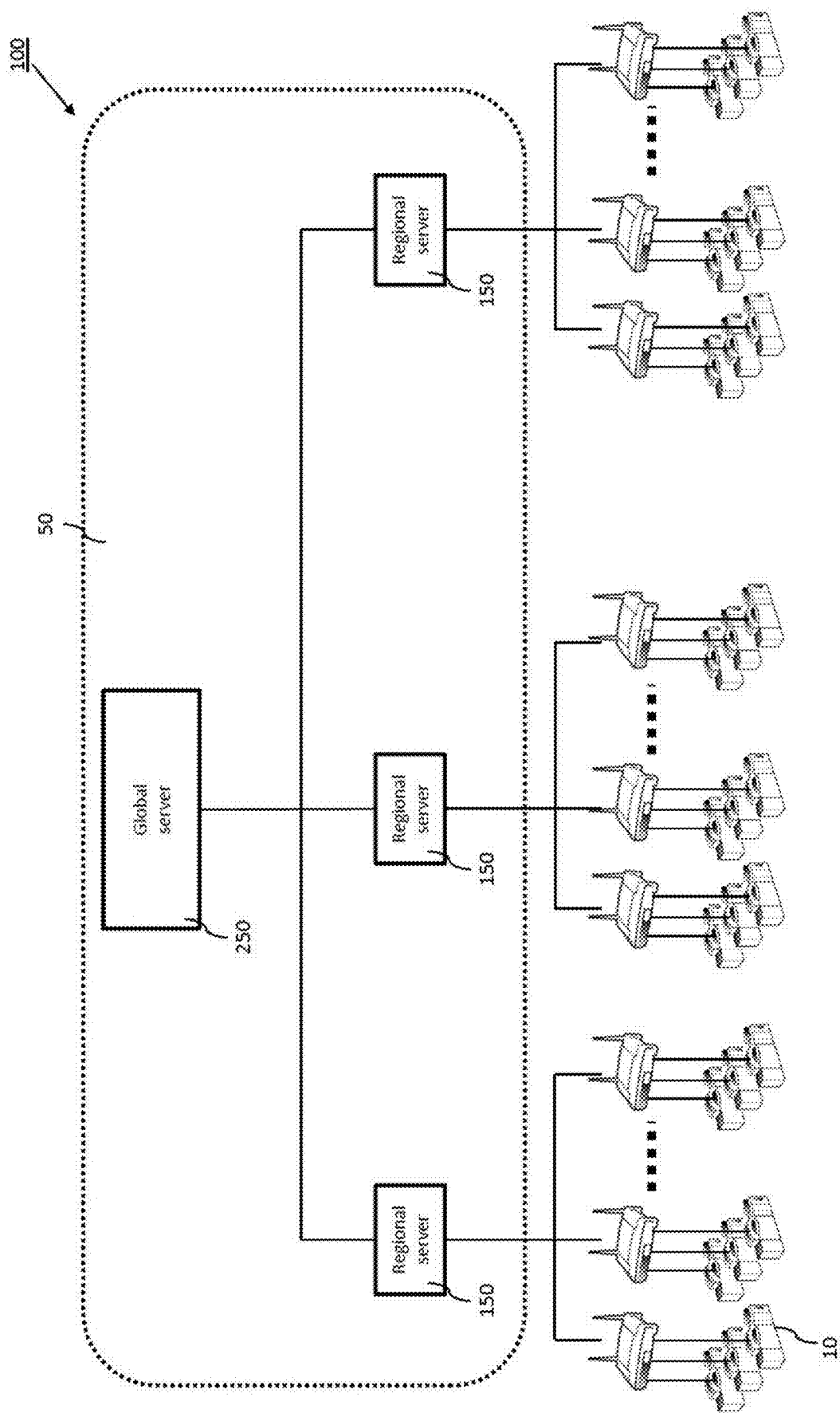
FIG. 4 illustrates a highly schematic block diagram of the disclosed laboratory system according to another embodiment of the present disclosure.

Turning now to FIG. 4, embodiments of the disclosed system and corresponding method are disclosed which address the need to have a remote maintenance system offering a balance between availability of context data (for predictive/prescriptive maintenance and mitigation) and privacy and regulatory limitations of its availability at regional respectively global level. FIG. 4 shows a highly schematic block diagram of a further embodiment of the disclosed laboratory system 100, wherein the remote maintenance system 50 can comprise a plurality of regional servers 150 each communicatively connected to a plurality of data collection components 20.1, 20.2.

Embodiments of the disclosed method corresponding to remote maintenance system 50 comprising one or more regional server(s) 150 each communicatively connected to a plurality of data collection components 20.1, 20.2, can further comprise the step of each regional server 150 analyzing operational parameters common to all and/or common to a subset of laboratory instruments 10 connected to the particular regional server 150 in order to detect correlation(s) between operational data and anomaly(s) specific to the respective region. Such a method/system can be advantageous as it can allow detection of correlations between anomalies and context data specific to a region but common to several groups of laboratory instruments within the region. For example, it has been observed that a certain consumable occasionally resulted in out of range analytical test results. Upon investigation at each data collection component, it has been determined that the out-of-range result was occurring at several locations (groups of laboratory instruments), but only in a specific region. After further investigation by a regional server, it was determined; that the package insert corresponding to a certain reagent lot delivered to a particular region having a particular language had a translation error regarding a dilution factor. The predictive rule in this case was determined to be a condition checking the lot number of reagents used by any of the laboratory instruments. The prescriptive action corresponding to this anomaly can be to provide an updated package insert with corrected translation. In the cases where wrongly diluted reagents were already loaded into laboratory instruments (hence the anomaly could not be avoided anymore), the corresponding mitigation action can be to stop processing any more samples using such reagents and to flag any test results as invalid. As this example shows, having an "abstraction" level for a particular region can be advantageous in determining correlations, predictive rules, prescriptive and mitigation actions applicable to an entire region. Further regional factors can comprise common regulatory constrains to groups of laboratory instruments 10 in a region, common transportation and storage conditions of consumables and/or common environmental factors affecting the operation of laboratory instruments (for example, increased humidity, high altitude such as, e.g., Mexico City).

Further shown on FIG. 4 is a global server 250 communicatively connected to a plurality of regional servers 150. The terms global and regional can be to be interpreted in a relative way, that is a global server 250 can be communicatively connected to a larger number of groups of laboratory instruments 10 (via the regional servers and the respective data collection components) than the regional server 150. The terms global and regional can comprise a geographical and/or logical grouping. Embodiments of the disclosed method corresponding to the hierarchically organized remote maintenance system 50 further comprising a global server 250 communicatively connected to a plurality of regional servers 150 can further comprise the steps of:

- each regional server 150 filtering out regionally sensitive data from the operational data;
- each of the plurality of regional servers 150 transmitting the filtered operational data to the global server 250; and
- the global server 250 analyzing operational parameters common to all laboratory instruments 10 of the laboratory system 100 in order to detect globally relevant correlation(s) between operational data and anomaly(s) irrespective of region.

Global factors which can be irrespective of region comprise (but not limited to) design or manufacturing parameters affecting operation of any laboratory instrument of a kind, globally common maintenance and operation processes and/or globally common software versions of laboratory instruments and/or insights (e.g., in the service organization of the provider of the laboratory instruments) generated after the launch of the respective laboratory instrument(s).

Further disclosed is a computer program product comprising instructions which, when executed by a remote maintenance system 50 and a plurality of data collection components 20.1, 20.2 of a laboratory system 100 comprising a first group 1 and second group 2 of laboratory instruments 10 for processing biological samples, the plurality of data collection components 20.1, 20.2 communicatively connected to the first group 1 or the second group 2 of laboratory instruments 10 and the remote maintenance system 50 communicatively connected to the data collection components 20.1, 20.2, wherein the first group 1 of laboratory instruments 10 can be connected to a first data collection component 20.1 while the second group 2 of laboratory instruments 10 can be connected to a second data collection component 20.2, can cause the laboratory system 100 to perform the steps of any one of the methods disclosed herein. Thus, specifically, one, more than one or even all of method steps as disclosed herein may be performed by using a computer or a computer network (such as a cloud computing service) or any suitable data processing equipment. As used herein, a computer program product can refer to the program as a tradable product. The product may generally exist in any format, such as in a downloadable file, on a computer-readable data carrier on premise or located at a remote location (cloud). The computer program product may be stored on a non-transitory computer-readable data carrier, a server computer as well as on transitory computer-readable data carrier such as a data carrier signal. Specifically, the computer program product may be distributed over a data network. Furthermore, not only the computer program product, but also the execution hardware may be located on premise or in a remotely, such as in a cloud environment.

Further disclosed and proposed is a non-transitory computer-readable storage medium comprising instructions which, when executed by a remote maintenance system 50 of a laboratory system 100 comprising a first group 1 and second group 2 of laboratory instruments 10 for processing biological samples, a plurality of data collection components 20.1, 20.2 communicatively connected to the first group 1 or the second group 2 of laboratory instruments 10 and a remote maintenance system 50 communicatively connected to the data collection components 20.1, 20.2, can cause the laboratory system 100 to perform the steps of any one of the methods disclosed herein.

Further disclosed and proposed is a modulated data signal comprising instructions which, when executed by a remote maintenance system 50 of a laboratory system 100 comprising a first group 1 and second group 2 of laboratory instruments 10 for processing biological samples, a plurality of data collection components 20.1, 20.2 communicatively connected to the first group 1 or the second group 2 of laboratory instruments 10 and a remote maintenance system 50 communicatively connected to the data collection components 20.1, 20.2, can cause the laboratory system 100 to perform the steps of any one of the methods disclosed herein.

According to some embodiments, operational data from the laboratory instruments 10 can be collected by the data collection components 20.1, 20.2 connected to the first group 1 of laboratory instruments 10 and second group 2 of laboratory instruments 10, the operational data being indicative of one or more operational parameters of the respective laboratory instruments 10. An anomaly related to one or more of the plurality of laboratory instruments 10 of the first group 1 can be detected by the first of the plurality of data collection components 20.1 connected to the first group 1 of laboratory instruments 10 based on the collected operational data. Context data can be transmitted by the first of the plurality of data collection components 20.1 to the remote maintenance system 50 upon detection of an anomaly, the context data comprising operational data and data indicative of the anomaly. One or more correlation(s) between the operational data and the anomaly(s) can be determined at the remote maintenance system 50. One or more correlation(s) can be validated at the remote maintenance system 50. One or more predictive rules corresponding to validated correlations can be determined at the remote maintenance system 50. One or more predictive rule(s) can be transmitted by the remote maintenance system 50 to data collection components 20.1, 20.2 connected to the first group 1 of laboratory instruments 10 and second group 2 of laboratory instruments 10. Occurrence of an anomaly of one or more of the plurality of laboratory instruments 10 of at least the second group 2 of laboratory instruments can be predicted based on the one or more predictive rule(s) by the second of the plurality of data collection components 20.2 connected to the second group 2 of laboratory instruments 10.

According to an example, operational data from the laboratory instruments 10 can be collected by the first of the plurality of data collection components 20.1 connected to the first group 1 of laboratory instruments for the detection of the anomaly, transmission of context data, determination of one or more correlation(s) between the operational data and the anomaly(s), validation of one or more correlation(s), and determination of one or more predictive rules corresponding to validated correlations. Operational data from the laboratory instruments 10 can be collected by the second of the plurality of data collection components 20.2 connected to the second group 2 of laboratory instruments for the prediction of an occurrence of an anomaly of one or more of the plurality of laboratory instruments 10 of at least the second group 2 of laboratory instruments based on the one or more predictive rule(s) by the second of the plurality of data collection components 20.2 connected to the second group 2 of laboratory instruments 10.

According to an example, operational data from the laboratory instruments 10 can be collected by the first of the plurality of data collection components 20.1 connected to the first group 1 of laboratory instruments, the operational data being indicative of one or more operational parameters of the respective laboratory instruments 10. An anomaly related to one or more of the plurality of laboratory instruments 10 of the first group 1 can be detected by the first of the plurality of data collection components 20.1 connected to the first group 1 of laboratory instruments 10 based on the collected operational data. Context data can be transmitted by the first of the plurality of data collection components 20.1 to the remote maintenance system 50 upon detection of an anomaly, the context data comprising operational data and data indicative of the anomaly. One or more correlation(s) between the operational data and the anomaly(s) can be determined at the remote maintenance system 50. One or more correlation(s) can be validated at the remote maintenance system 50. One or more predictive rules corresponding to validated correlations can be determined at the remote maintenance system 50. One or more predictive rule(s) can be transmitted by the remote maintenance system 50 to data collection components 20.1, 20.2 connected to the first group 1 of laboratory instruments 10 and second group 2 of laboratory instruments 10. Operational data from the laboratory instruments 10 can be collected by the second of the plurality of data collection components 20.2 connected to the second group 2 of laboratory instruments, the operational data being indicative of one or more operational parameters of the respective laboratory instruments 10, and used for the prediction of an occurrence of an anomaly of one or more of the plurality of laboratory instruments 10 of at least the second group 2 of laboratory instruments based on the one or more predictive rule(s) by the second of the plurality of data collection components 20.2 connected to the second group 2 of laboratory instruments 10.

According to some embodiments, operational data from the laboratory instruments 10 can be collected by the data collection components connected to the first group 1 of laboratory instruments 10, connected to the second group 2 of laboratory instruments 10, and connected to a third group of laboratory instruments, the operational data being indicative of one or more operational parameters of the respective laboratory instruments 10. An anomaly related to one or more of the plurality of instruments 10 of the first group 1 can be detected by the first of the plurality of data collection components 20.1 connected to the first group 1 of laboratory instruments 10 based on the collected operational data and/or an anomaly related to one or more of the plurality of instruments 10 of the second group 2 can be detected by the second of the plurality of data collection components 20.2 connected to the second group 2 of laboratory instruments 10 based on the collected operational data. Context data can be transmitted by the first of the plurality of data collection components 20.1 and/or by the second of the plurality of data collection components 20.2 to the remote maintenance system 50 upon detection of an anomaly, the context data comprising operational data and data indicative of the anomaly. One or more correlation(s) between the operational data and the anomaly(s) can be determined at the remote maintenance system 50. One or more correlation(s) can be validated at the remote maintenance system 50. One or more predictive rules corresponding to validated correlations can be determined at the remote maintenance system 50. One or more predictive rule(s) can be transmitted by the remote maintenance system 50 to the data collection components connected to the first group 1 of laboratory instruments 10, connected to the second group 2 of laboratory instruments 10, and connected to the third group of laboratory instruments. Occurrence of an anomaly of one or more of the plurality of laboratory instruments of at least the third group of laboratory instruments can be predicted based on the one or more predictive rule(s) by a third of the plurality of data collection components connected to the third group of laboratory instruments 10.

According to an example, operational data from the laboratory instruments 10 can be collected by the data collection components 20.1, 20.2 connected to the first group 1 of laboratory instruments 10 and second group 2 of laboratory instruments 10 for the detection of the anomaly(s), transmission of context data, determination of one or more correlation(s) between the operational data and the anomaly(s), validation of one or more correlation(s), and determination of one or more predictive rules corresponding to validated correlations. Operational data from the laboratory instruments can be collected by the third of the plurality of data collection components connected to the third group of laboratory instruments for the prediction of an occurrence of an anomaly of one or more of the plurality of laboratory instruments of at least the third group of laboratory instruments based on the one or more predictive rule(s) by the third of the plurality of data collection components connected to the third group of laboratory instruments.

According to some embodiments, the one or more of the plurality of data collection components 20.1, 20.2 connected to the first group 1 of laboratory instruments 10 and the second group 2 of laboratory instruments 10 can transmit data indicative of the failure of the one or more predictive rule(s) to the remote maintenance system 50 if an anomaly has been detected but not predicted. And/or one or more of the plurality of data collection components 20.1, 20.2 connected to the first group 1 of laboratory instruments 10 and the second group 2 of laboratory instruments 10 can transmit data to the remote maintenance system 50 indicative of the success of the predictive rule(s) that predicted the anomaly such as, for example, if the prediction of the anomaly has been confirmed. The remote maintenance system 50 can evaluates the data indicative of the success or the failure of predictive rule(s), can flag the predictive rule(s) with data indicative of the success outweighing data indicative of the failure as effective, and can flag the predictive rule(s) with data indicative of the failure outweighing data indicative of the success as ineffective. The remote maintenance system 50 can instruct the plurality of data collection components 20.1, 20.2 connected to the first group 1 of laboratory instruments 10 and the second group 2 of laboratory instruments 10 to discard the predictive rule(s) flagged as ineffective.

According to some embodiments, one or more prescriptive maintenance action(s) corresponding to the anomaly can be determined at the remote maintenance system 50. The one or more prescriptive maintenance action(s) comprising instruction(s) which, when executed with respect to one or more of the laboratory instruments 10, can reduce the probability of occurrence of the anomaly. One or more prescriptive maintenance action(s) can be transmitted from the remote maintenance system 50 to the plurality of data collection components 20.1, 20.2 connected to the first group 1 of laboratory instruments 10 and second group 2 of laboratory instruments 10. One or more of the plurality of collection components 20.1, 20.2 connected to the first group 1 of laboratory instruments 10 and second group 2 of laboratory instruments 10 can trigger execution of the one or more prescriptive maintenance action(s) upon predicting occurrence of an anomaly, comprising instructing one or more of the laboratory instruments 10 to execute the one or more prescriptive maintenance action(s) and/or providing the prescriptive maintenance action(s) to an operator.

According to some embodiments, data indicative of the success of the prescriptive maintenance actions can be transmitted to the remote maintenance system 50 if the anomaly could not be detected by the data collection component 20.1, 20.2 that triggered execution of the one or more prescriptive maintenance action(s). Data indicative of the failure of the prescriptive maintenance actions can be transmitted to the remote maintenance system 50 if the anomaly has been detected by the data collection component 20.1, 20.2 that triggered execution of the one or more prescriptive maintenance action(s). The remote maintenance system 50 can evaluate the data indicative of the success or the failure of prescriptive maintenance actions, can flag the prescriptive maintenance action(s) with data indicative of the success outweighing data indicative of the failure as effective, and can flag prescriptive maintenance action(s) with data indicative of the failure outweighing data indicative of the success as ineffective. The remote maintenance system 50 can instruct the plurality of data collection components 20.1, 20.2 connected to the first group 1 of laboratory instruments 10 and the second group 2 of laboratory instruments 10 to discard prescriptive maintenance action(s) flagged as ineffective.

According to some embodiments, one or more anomaly mitigation action(s) corresponding to the anomaly can be determined at the remote maintenance system 50. The one or more anomaly mitigation action(s) comprising instruction(s) which, when executed by one or more of the laboratory instruments 10, can mitigate the negative effects of the anomaly. One or more mitigation action(s) can be transmitted from the remote maintenance system 50 to the plurality of data collection components 20.1, 20.2 connected to the first group 1 of laboratory instruments 10 and second group 2 of laboratory instruments 10. The data collection component 20.1, 20.2 can trigger execution of the one or more anomaly mitigation action(s) if the anomaly has been detected by the collection component 20.1, 20.2, which instructed the one or more of the laboratory instruments 10 to execute the one or more prescriptive maintenance action(s).

According to some embodiments, data indicative of the success of the mitigation action(s) can be transmitted from the plurality of data collection components 20.1, 20.2 connected to the first group 1 of laboratory instruments 10 and the second group 2 of laboratory instruments 10 to the remote maintenance system 50 if the negative effects of the anomaly have been mitigated. Data indicative of the failure of the mitigation action(s) can be transmitted to the remote maintenance system 50 if the negative effects of the anomaly could not be mitigated. The remote maintenance system 50 can consolidate the data indicative of the success or the failure of mitigation action(s), can flag mitigation action(s) with data indicative of the success outweighing data indicative of the failure as effective, and can flag mitigation action(s) with data indicative of the failure outweighing data indicative of the success as ineffective. The remote maintenance system 50 can instruct the plurality of data collection components 20.1, 20.2 connected to the first group 1 of laboratory instruments 10 and the second group 2 of laboratory instruments 10 to discard mitigation action(s) flagged as ineffective.

According to some embodiments, the step of detecting an anomaly related to one or more of the plurality of laboratory instruments 10 can comprise:

- detecting deviation(s) of one or more operating parameters of the laboratory instrument 10 from manufacturer's operational ranges;
- detecting deviation(s) of one or more environmental parameters around the laboratory instrument 10 based on data captured by one or more sensors 12 located in the proximity of but outside the laboratory instrument 10 and communicatively connected to one of the plurality of data collection components 20.1, 20.2 connected to the first group 1 of laboratory instruments 10 and second group 2 of laboratory instruments 10.

According to some embodiments, the maintenance method can further comprise the step of increasing the frequency and/or volume and/or selection of parameters of the operational data from the laboratory instruments 10 captured by the data collection components 20.1, 20.2 connected to the first group 1 of laboratory instruments 10 and second group 2 of laboratory instruments 10 upon predicting occurrence of an anomaly.

According to some embodiments, the remote maintenance system 50 can comprise one or more regional server(s) 150 each communicatively connected to a plurality of data collection components 20.1, 20.2. The remote maintenance system 50 can further comprise each regional server 150 can be configured to analyze operational parameters common to all and/or common to a subset of laboratory instruments 10 connected to the particular regional server 150 in order to detect correlation(s) between operational data and anomaly(s) specific to the respective region. According to some embodiments, each of the plurality of data collection components 20.1, 20.2 communicatively connected to a regional server 150 can be dedicated for a specific group of laboratory instruments.

A maintenance method is proposed for a laboratory system. The laboratory system can comprise a first group and a second group of laboratory instruments for processing biological samples, a plurality of data collection components communicatively connected to the first group and the second group of laboratory instruments and a remote maintenance system communicatively connected to the data collection components. The maintenance method can comprise collecting operational data from the laboratory instruments by the data collection components. The operational data can be indicative of one or more operational parameters of the respective laboratory instruments. The maintenance method can also comprise detecting an anomaly related to one or more of the plurality of laboratory instruments of the first group by the first of the plurality of data collection components and transmitting context data by the first of the plurality of data collection components to the remote maintenance system upon detection of an anomaly. The context data can comprise operational data and data indicative of the anomaly. The maintenance method can also comprise determining one or more correlation(s) between the operational data and the anomaly(s) at the remote maintenance system; validating one or more correlation(s) at the remote maintenance system; determining at the remote maintenance system one or more predictive rules corresponding to validated correlations; transmitting the one or more predictive rule(s) by the remote maintenance system to the data collection components; and predicting occurrence of an anomaly of one or more of the plurality of laboratory instruments based on the one or more predictive rule(s) by one or more of the plurality of data collection components.

The maintenance method can further comprise one or more of the plurality of data collection components transmitting data indicative of the failure of the one or more predictive rule(s) to the remote maintenance system if an anomaly has been detected but not predicted and/or one or more of the plurality of data collection components transmitting data to the remote maintenance system indicative of the success of the predictive rule(s) that predicted the anomaly if the prediction of the anomaly has been confirmed. The remote maintenance system evaluating the data indicative of the success of the failure of predictive rule(s) by flagging predictive rule(s) with data indicative of the success outweighing data indicative of the failure as effective and flagging predictive rule(s) with data indicative of the failure outweighing data indicative of the success as ineffective. The remote maintenance system can instruct the plurality of data collection components to discard predictive rule(s) flagged as ineffective.

The maintenance method can further comprise determining at the remote maintenance system one or more prescriptive maintenance action(s) corresponding to the anomaly. The one or more prescriptive maintenance action(s) can comprise instruction(s) which, when executed with respect to one or more of the laboratory instruments, can reduce the probability of occurrence of the anomaly and can transmit the one or more prescriptive maintenance action(s) from the remote maintenance system to the plurality of data collection components. The one or more of the plurality of collection components can trigger the execution of the one or more prescriptive maintenance action(s) upon predicting occurrence of an anomaly comprising instructing one or more of the laboratory instruments to execute the one or more prescriptive maintenance action(s) and/or providing the prescriptive maintenance action(s) to an operator.

The maintenance method can further comprise transmitting data indicative of the success of the prescriptive maintenance actions to the remote maintenance system if the anomaly could not be detected by the data collection component, which triggered execution of the one or more prescriptive maintenance action(s) and transmitting data indicative of the failure of the prescriptive maintenance actions to the remote maintenance system if the anomaly has been detected by the data collection component which triggered execution of the one or more prescriptive maintenance action(s). The remote maintenance system can evaluate the data indicative of the success or the failure of prescriptive maintenance actions by flagging prescriptive maintenance action(s) with data indicative of the success outweighing data indicative of the failure as effective and flagging prescriptive maintenance action(s) with data indicative of the failure outweighing data indicative of the success as ineffective. The remote maintenance system can instruct the plurality of data collection components to discard prescriptive maintenance action(s) flagged as ineffective.

The prescriptive maintenance action(s) can comprise one or more of the following: updating software (SW) on the respective laboratory instrument, causing a redistribution of a workload between a plurality of laboratory instruments, redirecting of one or more biological samples from the laboratory instrument(s) corresponding to the predicted anomaly to laboratory instrument(s) other than the laboratory instrument(s) corresponding to the predicted anomaly, triggering replacement and/or service of one or more parts of the laboratory instrument(s) corresponding to the predicted anomaly, triggering calibration and/or quality control processes of the of the laboratory instrument(s) corresponding to the predicted anomaly, triggering the discarding of reagents and/or lots of reagents with a corresponding indication of improper handling and/or manufacturer recall, and/or triggering the discarding of laboratory instrument(s) with a corresponding indication of improper maintenance.

The maintenance method can further comprise determining at the remote maintenance system one or more anomaly mitigation action(s) corresponding to the anomaly, the one or more anomaly mitigation action(s) comprising instruction(s) which, when executed by one or more of the laboratory instruments, mitigate the negative effects of the anomaly and transmitting the one or more mitigation action(s) from the remote maintenance system to the plurality of data collection components. The data collection component can trigger execution of one or more anomaly mitigation action(s) if the anomaly has been detected by the data collection component, which instructed one or more of the laboratory instruments to execute the one, or more prescriptive maintenance action(s).

The maintenance method can further comprise transmitting data indicative of the success of the mitigation action(s) from the plurality of data collection components to the remote maintenance system if the negative effects of the anomaly have been mitigated and transmitting data indicative of the failure of the mitigation action(s) to the remote maintenance system if the negative effects of the anomaly could not be mitigated. The remote maintenance system can consolidate the data indicative of the success of the failure of mitigation action(s) by flagging mitigation action(s) with data indicative of the success outweighing data indicative of the failure as effective and flagging mitigation action(s) with data indicative of the failure outweighing data indicative of the success as ineffective. The remote maintenance system can further instruct the plurality of data collection components to discard mitigation action(s) flagged as ineffective.

The step of detecting an anomaly related to one or more of the plurality of laboratory instruments can comprise detecting deviation(s) of one or more operating parameters of the laboratory instrument from the manufacturer's operational ranges and can comprise detecting deviation(s) of one or more environmental parameters around the laboratory instrument based on data captured by one or more sensors located in the proximity of but outside the laboratory instrument and communicatively connected to one of the plurality of data collection components.

The maintenance method can further comprise increasing the frequency and/or volume and/or selection of parameters of the operational data from the laboratory instruments captured by the data collection components upon predicting occurrence of an anomaly.

The step of determining one or more correlation(s) between the operational data and the anomaly(s) at the remote maintenance system can comprise receiving input indicative of a correlation(s) between the operational data and the anomaly(s) and/or instructing a pattern recognition system to identify a correlation between the operational data and the same type of anomaly(s) based a database of operational data and anomalies related to the same or other of the plurality of laboratory instruments.

The step of validating one or more correlation(s) and marking the respective correlations as validated can comprises receiving input indicative of a validity of the correlation(s) between the operational data and the anomaly(s) and/or instructing a validation engine to validate the correlation(s) between the operational data and the anomaly(s).

The remote maintenance system can comprise one or more regional server(s). Each server can be communicatively connected to a plurality of data collection components. The method can further comprise the step of each regional server analyzing operational parameters common to all and/or common to a subset of laboratory instruments connected to the particular regional server in order to detect correlation(s) between operational data and anomaly(s) specific to the respective region.

The remote maintenance system can comprise a global server communicatively connected to a plurality of regional servers. The remote maintenance system can further comprise filtering out regionally sensitive data from the operational data by each regional server and transmitting the filtered operational data each of the plurality of regional servers to the global server. The global server can analyze operational parameters common to all laboratory instruments of the laboratory system in order to detect globally relevant correlation(s) between operational data and anomaly(s) irrespective of region.

A laboratory system is proposed. The laboratory system can comprise a first group of a plurality of laboratory instruments for processing biological samples communicatively connected to a first data collection component, a second group of a plurality of laboratory instruments for processing biological samples communicatively connected to a second data collection component, and a remote maintenance system communicatively connected to the plurality of data collection components. The laboratory system can be configured to carry out the above method.

A computer program product is proposed that comprises instructions which, when executed by a remote maintenance system of a laboratory system, wherein the laboratory system comprises a first group and second group of laboratory instruments for processing biological samples, a plurality of data collection components communicatively connected to the first group or the second group of laboratory instruments and a remote maintenance system communicatively connected to the data collection components, can cause the laboratory system to perform the above methods.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A maintenance method for a laboratory system, wherein the laboratory system comprises a first group and a second group of laboratory instruments for processing biological samples, a plurality of data collection components communicatively connected to the first group and second group of laboratory instruments, and a remote maintenance system communicatively connected to the data collection components, wherein the first group of laboratory instruments is connected to a first data collection component while the second group of laboratory instruments is connected to a second data collection component, the method comprising:
   collecting operational data from the laboratory instruments by the data collection components, the operational data being indicative of one or more operational parameters of the respective laboratory instruments;
   detecting an anomaly related to one or more of the plurality of laboratory instruments of the first group by the first of the plurality of data collection components based on the collected operational data;
   transmitting context data by the first of the plurality of data collection components to the remote maintenance system upon detection of an anomaly, the context data comprising operational data and data indicative of the anomaly;
   determining one or more correlation(s) between the operational data and the anomaly(s) at the remote maintenance system;
   validating the one or more correlation(s) at the remote maintenance system;
   determining at the remote maintenance system one or more predictive rules corresponding to validated correlations;
   transmitting the one or more predictive rule(s) by the remote maintenance system to the data collection components; and
   predicting occurrence of an anomaly of one or more of the plurality of laboratory instruments based on the one or more predictive rule(s) by one or more of the plurality of data collection components.

2. The maintenance method according to claim 1, further comprising,
   transmitting data indicative of failure of the one or more predictive rule(s) by one or more of the plurality of data collection components to the remote maintenance system if an anomaly has been detected but not predicted; and/or
   transmitting data by one or more of the plurality of data collection components to the remote maintenance system indicative of success of the predictive rule(s) that predicted the anomaly if the prediction of the anomaly has been confirmed;

evaluating the data indicative of success and failure of predictive rule(s) by the remote maintenance system by flagging predictive rule(s) with data indicative of success outweighing data indicative of failure as effective and flagging predictive rule(s) with data indicative of failure outweighing data indicative of success as ineffective; and instructing by the remote maintenance system the plurality of data collection components to discard predictive rule(s) flagged as ineffective.

3. The maintenance method according to claim 1, further comprising, determining at the remote maintenance system one or more prescriptive maintenance action(s) corresponding to the anomaly, the one or more prescriptive maintenance action(s) comprising instruction(s) which, when executed with respect to one or more of the laboratory instruments, reduce the probability of occurrence of the anomaly;

transmitting the one or more prescriptive maintenance action(s) from the remote maintenance system to the plurality of data collection components; and triggering execution of the one or more prescriptive maintenance action(s) upon predicting occurrence of an anomaly one or more of the plurality of collection components, comprising instructing one or more of the laboratory instruments to execute the one or more prescriptive maintenance action(s) and/or providing the prescriptive maintenance action(s) to an operator.

4. The maintenance method according to claim 3, further comprising, transmitting data indicative of success of the prescriptive maintenance actions to the remote maintenance system if the anomaly could not be detected by the data collection component which triggered execution of the one or more prescriptive maintenance action(s);

transmitting data indicative of failure of the prescriptive maintenance actions to the remote maintenance system if the anomaly has been detected by the data collection component which triggered execution of the one or more prescriptive maintenance action(s);

evaluating the data indicative of success or failure of prescriptive maintenance actions by the remote maintenance system (50) by flagging prescriptive maintenance action(s) with data indicative of success outweighing data indicative of failure as effective and flagging prescriptive maintenance action(s) with data indicative of failure outweighing data indicative of success as ineffective; and instructing the plurality of data collection components to discard prescriptive maintenance action(s) flagged as ineffective by the remote maintenance system.

5. The maintenance method according to claim 4, wherein the prescriptive maintenance action(s) comprise one or more of the following: updating software on the respective laboratory instrument, causing a redistribution of a workload between a plurality of laboratory instruments, redirecting of one or more biological samples from the laboratory instrument(s) corresponding to the predicted anomaly to laboratory instrument(s) other than the laboratory instrument(s) corresponding to the predicted anomaly, triggering replacement and/or service of one or more parts of the laboratory instrument(s) corresponding to the predicted anomaly, triggering calibration and/or quality control processes of the of the laboratory instrument(s) corresponding to the predicted anomaly, triggering the discarding of reagents and/or lots of reagents with a corresponding indication of improper handling and/or manufacturer recall, triggering the discarding of laboratory instrument(s) with a corresponding indication of improper maintenance, and triggering the automatic readjustment of laboratory instrument(s) or component(s) of the of laboratory instrument(s).

6. The maintenance method according to the claim 3, further comprising, determining at the remote maintenance system one or more anomaly mitigation action(s) corresponding to the anomaly, the one or more anomaly mitigation action(s) comprising instruction(s) which, when executed by one or more of the laboratory instruments, mitigate the negative effects of the anomaly;

transmitting the one or more mitigation action(s) from the remote maintenance system to the plurality of data collection components; and triggering by the data collection component execution of one or more anomaly mitigation action(s) if the anomaly has been detected by the data collection component which instructed one or more of the laboratory instruments to execute the one or more prescriptive maintenance action(s).

7. The maintenance method according to claim 6, further comprising, transmitting data indicative of success of the mitigation action(s) from the plurality of data collection components to the remote maintenance system if the negative effects of the anomaly have been mitigated;

transmitting data indicative of failure of the mitigation action(s) to the remote maintenance system if the negative effects of the anomaly could not be mitigated; and consolidating by the remote maintenance system the data indicative of success or failure of mitigation action(s) by flagging mitigation action(s) with data indicative of success outweighing data indicative of failure as effective and flagging mitigation action(s) with data indicative of failure outweighing data indicative of success as ineffective, wherein the remote maintenance system instructs the plurality of data collection components to discard mitigation action(s) flagged as ineffective.

8. The maintenance method according to claim 1, wherein detection of an anomaly related to one or more of the plurality of laboratory instruments comprises detecting deviation(s) of one or more operating parameters of the laboratory instrument from manufacturer's operational ranges and detecting deviation(s) of one or more environmental parameters around the laboratory instrument based on data captured by one or more sensors located in the proximity of but outside the laboratory instrument and communicatively connected to one of the plurality of data collection components.

9. The maintenance method according to claim 1, further comprising, increasing the frequency and/or volume and/or selection of parameters of the operational data from the laboratory instruments captured by the data collection components upon predicting occurrence of an anomaly.

10. The maintenance method according to claim 1, wherein the determination of one or more correlation(s) between the operational data and the anomaly(s) at the remote maintenance system comprises receiving input indicative of a correlation(s) between the operational data and the anomaly(s) and/or instructing a pattern recognition system to identify a correlation between the operational data and the same type of anomaly(s) based a database of operational data and anomalies related to the same or other of the plurality of laboratory instruments.

11. The maintenance method according to claim 1, wherein the validation of one or more correlation(s) and marking the respective correlations as validated comprises receiving input indicative of a validity of the correlation(s) between the operational data and the anomaly(s) and/or instructing a validation engine to validate the correlation(s) between the operational data and the anomaly(s).

12. The maintenance method according to claim 1, wherein the remote maintenance system comprises one or more regional server(s) each communicatively connected to a plurality of data collection components, the method further comprising analyzing by each regional server operational parameters common to all and/or common to a subset of laboratory instruments connected to the particular regional server in order to detect correlation(s) between operational data and anomaly(s) specific to the respective region.

13. The maintenance method according to claim 12, wherein the remote maintenance system comprises a global server communicatively connected to a plurality of regional servers, the method further comprising filtering out regionally sensitive data from the operational data by each regional server, transmitting the filtered operational data each of the plurality of regional servers to the global server, and analyzing by the global server operational parameters common to all laboratory instruments of the laboratory system in order to detect globally relevant correlation(s) between operational data and anomaly(s) irrespective of region.

14. A laboratory system, the laboratory system comprising:
a first group of a plurality of laboratory instruments for processing biological samples communicatively connected to a first data collection component;
a second group of a plurality of laboratory instruments for processing biological samples communicatively connected to a second data collection component; and
a remote maintenance system communicatively connected to the plurality of data collection components, wherein the laboratory system is configured to carry out the method according to claim 1.

15. A computer program product comprising instructions which, when executed by a remote maintenance system and a plurality of data collection components of a laboratory system comprising a first group and second group of laboratory instruments for processing biological samples, the plurality of data collection components communicatively connected to the first group and second group of laboratory instruments and the remote maintenance system communicatively connected to the data collection components, wherein the first group of laboratory instruments is connected to a first data collection component while the second group of laboratory instruments is connected to a second data collection component, cause the laboratory system to perform the method according to claim 1.

* * * * *